United States Patent
Takeuchi et al.

(10) Patent No.: US 6,190,805 B1
(45) Date of Patent: Feb. 20, 2001

(54) POLYMERIZABLE COMPOUND, SOLID POLYMER ELECTROLYTE USING THE SAME AND USE THEREOF

(75) Inventors: Masataka Takeuchi; Shuichi Naijo; Takashi Ohkubo; Ayako Nishioka; Masaaki Nishioka, all of Chiba (JP)

(73) Assignee: Showa Denko Kabushiki Kaisha, Tokyo (JP)

( * ) Notice: Under 35 U.S.C. 154(b), the term of this patent shall be extended for 0 days.

(21) Appl. No.: 09/149,093

(22) Filed: Sep. 8, 1998

Related U.S. Application Data

(60) Provisional application No. 60/071,117, filed on Jan. 13, 1998.

(30) Foreign Application Priority Data

Sep. 10, 1997 (JP) ........................................ 9-245613
Apr. 28, 1998 (JP) ................................. 10-119246

(51) Int. Cl.[7] .................... H01M 10/40; C07C 69/96; H01G 9/022
(52) U.S. Cl. ...................... 429/307; 429/317; 361/525; 558/265
(58) Field of Search ................... 429/307, 317; 558/265; 361/525

(56) References Cited

U.S. PATENT DOCUMENTS

| | | | | |
|---|---|---|---|---|
| 4,119,106 | * | 10/1978 | Grubbs et al. | 558/265 |
| 4,273,726 | * | 6/1981 | Altuglu | 552/265 |
| 4,906,537 | * | 3/1990 | Hotani et al. | 429/317 |
| 5,276,174 | * | 1/1994 | Plotkin et al. | 558/265 X |
| 5,407,593 | * | 4/1995 | Whang | 429/317 |
| 6,015,638 | * | 1/2000 | Ventura et al. | 429/307 |

FOREIGN PATENT DOCUMENTS

| | | |
|---|---|---|
| 58-36828 | 3/1983 | (JP) . |
| 62-272161 | 11/1987 | (JP) . |
| 63-244570 | 10/1988 | (JP) . |
| 4-253771 | 9/1992 | (JP) . |
| 6-140052 | 5/1994 | (JP) . |
| 6-187822 | 8/1994 | (JP) . |
| 8-295715 | 11/1996 | (JP) . |
| 9-147912 | 6/1997 | (JP) . |

\* cited by examiner

Primary Examiner—Stephen Kalafut
(74) Attorney, Agent, or Firm—Sughrue, Mion, Zinn Macpeak & Seas, PLLC.

(57) ABSTRACT

The polymer compound of the present invention which contains a poly- or oligo-carbonate group and is preferably obtained by utilizing a polymerization reaction using a polymerizable functional group represented by formula (2) and/or formula (3) below:

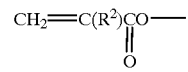

(2)

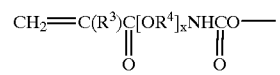

(3)

exhibits good strength even when it is formed into a thin film and has high ion conductivity and excellent workability. By the use of this polymer compound, solid polymer electrolyte, battery and/or electric double layer capacitor having high-temperature characteristics and large current characteristics are provided.

34 Claims, 1 Drawing Sheet

POLYMERIZABLE COMPOUND, SOLID POLYMER ELECTROLYTE USING THE SAME AND USE THEREOF

This application claims benefit of the provisional application No. 60/071117 filed Jan. 13, 1998.

FIELD OF THE INVENTION

The present invention relates to a solid polymer electrolyte comprising a polymer compound containing a poly- or oligo-carbonate group as a main component, and an electrolyte salt, which is useful for various electrochemical elements, and a production process thereof, a battery using the solid polymer electrolyte and a production process thereof, and an electric double layer capacitor using the solid polymer electrolyte and a production method thereof.

BACKGROUND OF THE INVENTION

To keep up with the trend in the ionics field toward downsizing and entirely solid formation, attempts are being aggressively made to apply an entirely solid primary battery, secondary battery or electric double layer capacitor using a solid electrolyte to electrochemical elements, as a new ion conductor which can take the place of conventional electrolytic solutions.

More specifically, electrochemical elements using a conventional electrolytic solution are deficient in the long-term reliability because liquid leakage outside the component or elution of the electrode active material is readily caused. However, products using a solid electrolyte are free of such a problem and can be easily formed to have a small thickness. Furthermore, the solid electrolyte has excellent heat resistance and is advantageous also in the manufacturing process of a product such as a battery.

In particular, when a solid polymer electrolyte mainly comprising a polymer compound is used, the battery can have increased flexibility as compared with those using an inorganic material and accordingly, can be formed into various shapes. However, batteries heretofore investigated have a problem that due to low ion conductivity of the solid polymer electrolyte, the takeout current is small.

In recent years, many studies have been made on lithium secondary batteries using a metal oxide or metal sulfide such as $LiCoO_2$, $LiNiO_2$, $LiMnO_2$ and $MoS_2$ for the positive electrode, and lithium, lithium alloy, a carbon material, inorganic compound or polymer compound capable of occluding and releasing lithium ion for the negative electrode. For example, *J. of Electrochem. Soc.*, vol. 138 (No. 3), page 665 (1991) reports a battery using $MnO_2$ or $NiO_2$ for the positive electrode. This is high in the capacity per weight or per volume and drawing attention.

Further, an electric double layer capacitor comprising polarizable electrodes formed of a carbon material having a large specific area, such as activated carbon or carbon black, having disposed therebetween an ion conductive solution is often used in these days as a memory backup power source. For example, *Kino Zairyo* (*Functional Materials*), page 33, (February, 1989) describes a capacitor using carbon-base polarizable electrodes and an organic electrolytic solution; and 13*th Electrochemical Society Meeting Atlanta Ga.*, No. 18 (May, 1988) describes an electric double layer capacitor using an aqueous sulfuric acid solution.

Further, JP-A-63-244570 (the term "JP-A" as used herein means an "unexamined published Japanese patent application") discloses a capacitor using $Rb_2Cu_3I_3Cl_7$ having high electrical conductivity as an inorganic solid electrolyte.

However, the battery or electric double layer capacitor using an existing electrolytic solution is deficient in the long-term use or reliability because liquid leakage outside the battery or capacitor is readily caused under an abnormal condition such as when the battery or capacitor is used for a long period of time or a high voltage is applied. On the other hand, the battery or electric double layer capacitor using a conventional inorganic ion conductive material has a problem that the ion conductive material is low in the decomposition voltage and accordingly, the output voltage is low, or has a problem in the production process because an interface between the electrolyte and the electrode is difficult to form.

JP-A-4-253771 proposes to use a polyphosphazene-base polymer compound as an ion conductive material of a battery or electric double layer capacitor. The battery or electric double layer capacitor using a solid ion conductive material mainly comprising such a polymer compound is advantageous in that the output voltage is high as compared with those using an inorganic ion conductive material and it can be formed into various shapes and easily sealed. However, in this case, the ion conductivity of the solid polymer electrolyte is not sufficiently high and it is approximately from $10^{-4}$ to $10^{-6}$ S/cm, as a result, the takeout current is disadvantageously small. Furthermore, in assembling a solid electrolyte together with polarizable electrodes in a capacitor, it is difficult to uniformly compound the solid electrolyte with the carbon material having a large specific area because the materials mixed are both a solid.

The solid polymer electrolytes under general investigations are improved in the ion conductivity up to approximately from $10^{-4}$ to $10^{-5}$ S/cm at room temperature, however, this still stays in a level lower by two figures than that of the liquid ion conductive material. Further, at low temperatures of 0° C. or less, the ion conductivity generally lowers to an extreme extent. Furthermore, when the solid electrolyte is compounded and assembled with an electrode of an element such as a battery or electric double layer capacitor or when the solid electrolyte is formed into a thin film and assembled in an element such as a battery or electric double layer capacitor, difficult techniques are necessary for the working of compounding or continuously contacting the solid polymer electrolyte with an electrode, thus, a problem is also present in the process of producing an element.

As an example of the solid polymer electrolyte, *Br. Polym. J.*, Vol. 319, page 137 (1975) reports that a composite material of a polyethylene oxide with an inorganic alkali metal salt exhibits ion conductivity, but the ion conductivity thereof at room temperature is as low as $10^{-7}$ S/cm.

Many reports have been issued in recent years stating that a comb-type polymer having introduced into the side chain thereof oligooxyethylene is intensified in the thermal mobility of oxyethylene chain which undertakes the ion conductivity, and thereby improved in the ion conductivity.

For example, *J. Phys. Chem.*, Vol. 89, page 987 (1984) describes an example where oligooxyethylene is added to the side chain of polymethacrylic acid and an alkali metal salt is compounded thereto. Further, *J. Am. Chem. Soc.*, Vol. 106, page 6854 (1984) describes polyphosphazene having an oligooxyethylene side chain, compounded with an alkali metal salt, however, the ion conductivity is about $10^{-5}$ S/cm and still insufficient.

U.S. Pat. No. 4,357,401 reports that a solid polymer electrolyte comprising a salt ionizable with a cross-linked polymer having a hetero atom is reduced in the crystallinity, has a low glass transition point and is improved in the ion conductivity, but the ion conductivity is about $10^{-5}$ S/cm and still insufficient.

*J. Appl. Electrochem.*, Vol. 5, pp. 63–69 (1975) reports that a so-called polymer gel electrolyte obtained by adding a solvent and an electrolyte to a cross-linked polymer compound, such as polyacrylonitrile or polyvinylidene fluoride gel, has a high ion conductivity. Further, JP-B-58-36828 (the term "JP-B" as used herein means an "examined Japanese patent publication") reports that a polymer compound gel electrolyte similarly obtained by adding a solvent and an electrolyte to a polymethacrylic acid alkyl ester has a high ion conductivity.

However, despite the high ion conductivity, these polymer gel electrolytes are disadvantageous in that due to the fluidity imparted, they cannot be handled as a complete solid, have poor film strength or film formability, readily cause short circuit when applied to an electric double layer capacitor or a battery, and have a problem in view of sealing similar to the case of using a liquid ion conductive material.

U.S. Pat. No. 4,792,504 proposes to improve the ion conductivity by using a cross-linked solid polymer electrolyte where the continuous network of polyethylene oxide is impregnated with an electrolytic solution comprising a metal salt and an aprotic solvent. However, the ion conductivity is $10^{-4}$ S/cm and still insufficient. Further, as a result of addition of a solvent, a problem arises that the film strength is reduced.

JP-B-3-73081 and its corresponding U.S. Patent (U.S. Pat. No. 4,908,283) disclose a process for forming a solid polymer electrolyte by irradiating an active ray such as ultraviolet ray, on a composition comprising an acryloyl-modified polyalkylene oxide such as polyethylene glycol diacrylate/an electrolyte salt/an organic solvent, thereby reducing the polymerization time.

Also, U.S. Pat. Nos. 4,830,939 and 5,037,712 disclose a process for forming a solid polymer electrolyte containing an electrolytic solution similarly by irradiating radiation such as ultraviolet ray or electron beam, on a composition comprising a cross-linking polyethylenic unsaturated compound/an electrolyte salt/a solvent inactive to active ray. In these systems, the ion conductivity is improved due to the increase of the electrolytic solution in the solid polymer electrolyte, however, it is still insufficient and the film strength is liable to decrease.

U.S. Pat. No. 5,609,974 discloses a solid polymer electrolyte using across-linked polymer compound having introduced thereinto a monocarbonate side chain so as to elevate the dissociation ability of the electrolyte salt, however, the amount of carbonate introduced is small and satisfactory capabilities such as ion conductivity and current characteristics cannot be obtained.

U.S. Pat. No. 5,001,023 describes an electrochemical device using as a component of solid polymer electrolyte a polymer to which a side chain having no active hydrogen atoms is bonded and mentions poly(ethylene-ether carbonate) with methacrylate terminal cap as an example of the said polymer. However, these polymers are insufficient in ion conductivity and cannot be polymerized when containing much solvent due to poor polymerizability of methacrylate, and have a problem in workability as a solid polymer electrolyte gel.

JP-A-9-147912 describes a solid polymer electrolyte which has flexibility as well as rigidity and is improved in affinity to metal electrodes and interfacial resistance by using a copolymer of poly(alkylene(ether) carbonate) with methacrylate terminal cap similar to that described in U.S. Pat. No. 5,001,023 and polyether with methacrylate terminal cap. However, they have a problem in durability of polyether chains and also have problems that the polymerization reaction unevenly proceeds because of the use of two or more methacrylates and that not a few double bonds remain since the polymerizability of methacrylate is not sufficient, which also causes a deficiency in durability.

JP-A-8-295715 proposes a solid polymer electrolyte which has improved ion conductivity and film-forming properties and exhibits less polymerization shrinking by using urethane acrylate having particular structures comprising polyether or polyester units. However, these compounds are synthesized through a reaction between a compound having hydroxyl groups at both its ends and a diisocyanate and contain many by-products. Accordingly, they have a problem in the stability of ion conductivity and electrochemical properties. Furthermore, there also remains a problem in durability since they contain polyether and/or polyester. This publication also mentions other structures in which polycarbonate is introduced in place of the polyether or the like but it does not give sufficient consideration to such properties like affinity to the electrodes, for the mentioned structures including those containing aromatic rings both in polycarbonate and diisocyanate, for instance. Further, this publication does not give any specific examples of the production of the solid polymer electrolyte with the use of a polymer containing polycarbonate chains and does not investigate the properties of such electrolyte.

*Solid State Ionics*, No. 7, page 75 (1982) reports that by further compounding an alumina particle to a $LiClO_4$/polyethylene oxide composite material as a solid polymer electrolyte, the strength of the solid polymer electrolyte can be improved without reducing the ion conductivity. WO94/06165 proposes a solid electrolyte comprising a polyalkylene oxide/isocyanate cross-linked entity/inorganic oxide composite material impregnated with a non-aqueous electrolytic solution, with the intention of increasing strength of the solid polymer electrolyte containing an electrolytic solution. However, these composite solid polymer electrolytes are not satisfied in the characteristics of the polymer compound itself and their practical use has a problem in view of the ion conductivity, workability and stability.

JP-A-62-272161 discloses an electric double layer capacitor comprising a combination of a solid polymer electrolyte using a polymer compound such as cyanoethyl cellulose with an activated carbon electrode, however, the solid polymer electrolyte used is insufficient in the ion conductivity and difficult to compound with the activated carbon electrode, and an electric double layer capacitor having satisfactory capabilities has not yet been obtained.

In order to solve these problems, the present inventors have proposed an ion conductive solid polymer electrolyte using a composite material comprising a polymer obtained from a (meth)acrylate prepolymer having a urethane bond and containing an oxyalkylene group, and an electrolyte salt (JP-A-6-187822). This solid polymer electrolyte has an ion conductivity of a high level such that in the state where a solvent is not added, the ion conductivity is $10^{-4}$ S/cm (at room temperature) and when a solvent is added, it increases to $10^{-3}$ S/cm or more even at room temperature or a temperature lower than that. Further, the film quality is good and improved to such a degree that the electrolyte can be obtained as a self-standing film. Furthermore, the prepolymer has good polymerizability and is advantageous in that when applied to a battery, it can be integrated into a battery in the state of a prepolymer and then polymerized into a solid.

However, this system has also a problem that the film strength is deficient for the use as a separator of a battery or the like and handling in an industrial scale is difficult. Further, the polymer, particularly the oxyalkylene moiety at a high temperature, is readily deteriorated due to a slight amount of impurities within the battery system, such as water content, decomposition product of the electrolyte salt or electrode material impurity, and this adversely affects the life of the battery.

Furthermore, there is a problem that when the system is applied to a battery or an electric double layer capacitor, the capacity is greatly reduced at the discharging of a large current. This is considered to occur because the dielectric constant of the polymer compound is still insufficient and accordingly, the electrolyte salt cannot dissociate or move satisfactorily within the solid polymer electrolyte.

SUMMARY OF THE INVENTION

An object of the present invention is to provide a solid polymer electrolyte having good strength even when it is formed into a thin film having a thickness on the order of tens of μm, having high ion conductivity, having excellent workability, high-temperature characteristics and large current characteristics, and being useful for various electrochemical elements, and a production process thereof.

Another object of the present invention is to provide a primary or secondary battery using the solid polymer electrolyte, which can be easily formed into a thin film, can work in high capacity and large current and has excellent workability and reliability, and a production process thereof.

Still another object of the present invention is to provide an electric double layer capacitor using the solid polymer electrolyte, which is high in the output voltage, large in the takeoff current and excellent in the workability and reliability, and a production process thereof.

As a result of extensive investigations to solve the above-described problems, the present inventors have found that a highly ion conductive solid polymer electrolyte comprising a polymer compound having a cross-linked and/or side chain group mainly comprising a poly- or oligo-carbonate group, and an electrolyte salt can be a solid polymer electrolyte having good film strength, high ion conductivity, excellent workability and superior large current characteristics and high-temperature characteristics as compared with conventional oligo-oxyalkyelne-base electrolytes.

Further, the present inventors have found that by using this solid polymer electrolyte, a primary or secondary battery which is easy to form into a thin film, works in high capacity and large current, and is excellent in the reliability and stability, can be fabricated.

Furthermore, the present inventors have found that by using this solid polymer electrolyte, an electric double layer capacitor having high output voltage, large takeout current and excellent workability, reliability and stability, can be obtained.

Based on these findings, the present inventors provide (1) a solid polymer electrolyte and a production process thereof, (2) a battery or electric double layer capacitor using the solid polymer electrolyte and a production process thereof, (3) and a polymerizable compound useful as the starting material of the polymer compound for the solid polymer electrolyte, which are described below.

That is, the present invention provides the following solid polymer electrolytes.

[1] A solid polymer electrolyte comprising at least one polymer compound having a poly- or oligo-carbonate group represented by formula (1):

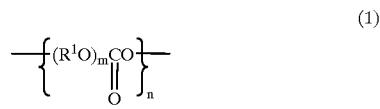

[wherein $R^1$ represents a chained, branched and/or cyclic divalent group having from 1 to 10 carbon atoms, which may contain a hetero atom, m represents an integer of from 3 to 10 and n represents an integer of from 2 to 1,000, provided that $R^1$, m and n which are present in plurality in the same molecule may be the same or different, respectively] and at least one electrolyte salt.

[2] The solid polymer electrolyte as described in the above 1, wherein the polymer compound contains a poly- or oligo-carbonate group represented by the general formula (1) and is obtained by utilizing a polymerization reaction using a polymerizable functional group represented by formula (2) and/or formula (3):

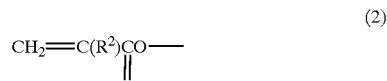

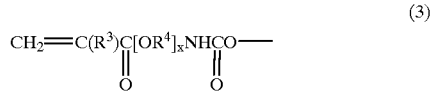

[wherein $R^2$ and $R^3$ each represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^2$, $R^3$, $R^4$ and x which are present in plurality in the same molecule may be the same or different, respectively].

[3] The solid polymer electrolyte as described in the above 1 or 2, which contains at least one organic solvent.

[4] The solid polymer electrolyte as described in the above 3, wherein the organic solvent is a carbonate-base compound.

[5] The solid polymer electrolyte as described in the above 1 or 2, which contains at least one inorganic oxide.

[6] The solid polymer electrolyte as described in the above 1 or 2, wherein the electrolyte salt is selected from an alkali metal salt, a quaternary ammonium salt and a quaternary phosphonium salt.

[7] A solid polymer electrolyte comprising:
 (i) at least one polymer compound which contains a poly- or oligo-carbonate group represented by formula (1):

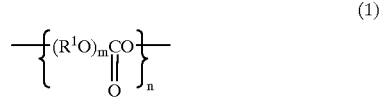

[wherein $R^1$ represents a chained, branched and/or cyclic divalent group having from 1 to 10 carbon atoms, which may contain a hetero atom, m represents an integer of from 3 to 10 and n represents an integer of from 2 to 1,000, provided that $R^1$, m and n which are present in plurality in the same molecule may be the same or different, respectively] and is obtained by utilizing a polymerization reaction using a polymerizable functional group represented by the following formula (2) and/or formula (3):

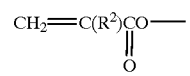
(2)

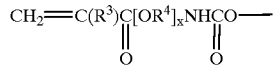
(3)

[wherein $R^2$ and $R^3$ each represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^2$, $R^3$, $R^4$ and x which are present in plurality in the same molecule may be the same or different, respectively];

(ii) at least one organic solvent;
(iii) at least one inorganic oxide; and
(iv) at least one electrolyte salt.

[8] The solid polymer electrolyte as described in the above 7, wherein the organic solvent is a carbonate-base compound.

[9] The solid polymer electrolyte as described in the above 7 or 8, wherein the electrolyte salt is selected from an alkali metal salt, a quaternary ammonium salt and a quaternary phosphonium salt.

[10] A solid polymer electrolyte comprising at least one polymer compound which contains a poly- or oligo-carbonate group represented by formula (1'):

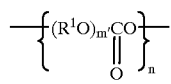
(1')

[wherein $R^1$ and n represent the same as in the general formula (1), m' represents 1 or 2, provided that $R^1$, m' and n which are present in plurality in the same molecule may be the same or different, respectively] and is obtained by utilizing a polymerization reaction using a polymerizable functional group represented by formula (3):

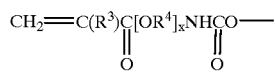
(3)

[wherein $R^3$, $R^4$ and x have the same meanings as in the above 2] and at least one electrolyte salt.

[11] The solid polymer electrolyte as described in the above 10, which contains at least one organic solvent.

[12] The solid polymer electrolyte as described in the above 11, wherein the organic solvent is a carbonate-base compound.

[13] The solid polymer electrolyte as described in the above 10, which contains at least one inorganic oxide.

[14] The solid polymer electrolyte as described in the above 10, wherein the electrolyte salt is selected from an alkali metal salt, a quaternary ammonium salt and a quaternary phosphonium salt.

[15] A solid polymer electrolyte comprising:
(i) at least one polymer compound which contains a poly- or oligo-carbonate group represented by formula (1'):

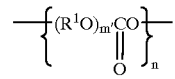
(1')

[wherein $R^1$ and n represent the same as in the general formula (1), m' represents an integer of from 1 or 2, provided that $R^1$, m' and n which are present in plurality in the same molecule may be the same or different, respectively] and is obtained by utilizing a polymerization reaction using a polymerizable functional group represented by formula (3):

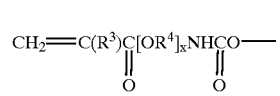
(3)

[wherein $R^3$, $R^4$ and x have the same meanings as in the above 2];

(ii) at least one organic solvent;
(iii) at least one inorganic oxide; and
(iv) at least one electrolyte salt.

[16] The solid polymer electrolyte as described in the above 15, wherein the organic solvent is a carbonate-base compound.

[17] The solid polymer electrolyte as described in the above 15 or 16, wherein the electrolyte salt is selected from an alkali metal salt, a quaternary ammonium salt and a quaternary phosphonium salt.

[18] A battery using the solid polymer electrolyte described in any one of the above 1 to 17.

[19] The lithium battery as described in the above 18, wherein the negative electrode used in the battery is at least one material selected from lithium, lithium alloy, a carbon material capable of occluding and releasing lithium ion, an inorganic oxide capable of occluding and releasing lithium ion, an inorganic chalcogenide capable of occluding and releasing lithium ion, and an electroconductive polymer compound capable of occluding and releasing lithium ion.

[20] An electric double layer capacitor comprising polarizable electrodes disposed through an ion conductive material, wherein the ion conductive material is a solid polymer electrolyte described in any one of the above 1 to 17.

The present invention also provides the following production process of a solid polymer electrolyte.

[21] A process for producing a solid polymer electrolyte, comprising disposing at least one heat and/or active ray polymerizable compound having a poly- or oligo-carbonate group represented by formula (1):

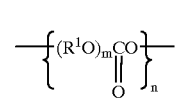
(1)

[wherein the symbols have the same meanings as in the above 1] and a polymerizable functional group represented by formula (2) and/or formula (3):

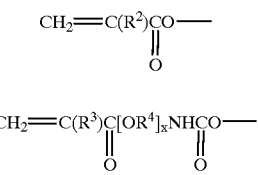
(2)

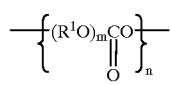
(3)

[wherein the symbols have the same meanings as in the above 2] and a polymerizable composition containing at least one electrolyte salt or further containing at least one organic solvent and/or at least one inorganic oxide on a support, and polymerizing the polymerizable composition.

[22] A process for producing a solid polymer electrolyte, comprising disposing at least one heat and/or active ray polymerizable compound having a poly- or oligo-carbonate group represented by formula (1):

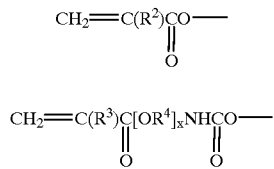
(1)

[wherein the symbols have the same meanings as in the above 1] and a polymerizable functional group represented by formula (2) and/or formula (3):

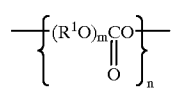
(2)

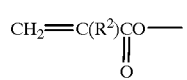
(3)

[wherein the symbols have the same meanings as in the above 2] and a polymerizable composition containing at least one organic solvent or further containing at least one inorganic oxide on a support, polymerizing the polymerizable composition, and contacting the polymer obtained with an electrolytic solution to impregnate an electrolyte salt.

The present invention also provides the following production process of a battery.

[23] A process for producing a battery, comprising placing at least one heat and/or active ray polymerizable compound having a poly- or oligo-carbonate group represented by formula (1):

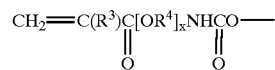
(1)

[wherein the symbols have the same meanings as in the above 1] and a polymerizable functional group represented by formula (2) and/or formula (3):

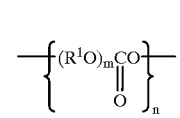
(2)

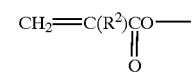
(3)

[wherein the symbols have the same meanings as in the above 2] and a polymerizable composition containing at least one electrolyte salt or further containing at least one organic solvent and/or at least one inorganic oxide in a structure for constructing a battery or disposing these on a support, and polymerizing the polymerizable composition.

[24] A process for producing a battery, comprising placing at least one heat and/or active ray polymerizable compound having a poly- or oligo-carbonate group represented by formula (1):

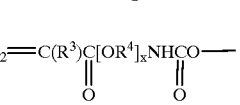
(1)

[wherein the symbols have the same meanings as in the above 1] and a polymerizable functional group represented by formula (2) and/or formula (3):

(2)

(3)

[wherein the symbols have the same meanings as in the above 2] and a polymerizable composition containing at least one organic solvent or further containing at least one inorganic oxide in a structure for constructing a battery or disposing these on a support, and contacting the polymer obtained with an electrolytic solution to impregnate an electrolyte salt.

The present invention also provides the following production process of an electric double layer capacitor.

[25] A process for producing an electric double layer capacitor, comprising placing at least one heat and/or active ray polymerizable compound having a poly- or oligo-carbonate group represented by formula (1):

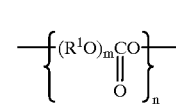
(1)

[wherein the symbols have the same meanings as in the above 1] and a polymerizable functional group represented by formula (2) and/or formula (3):

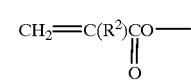
(2)

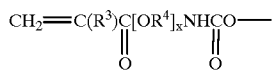

(3)

[wherein the symbols have the same meanings as in the above 2] and a polymerizable composition containing at least one electrolyte salt or further containing at least one organic solvent and/or at least one inorganic oxide in a structure for constructing an electric double layer capacitor or disposing these on a support, and polymerizing the polymerizable composition.

[26] A process for producing an electric double layer capacitor, comprising placing at least one heat and/or active ray polymerizable compound having a poly- or oligo-carbonate group resented by formula (1):

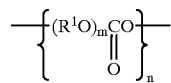

(1)

[wherein the symbols have the same meanings as in the above 1] and a polymerizable functional group represented by formula (2) and/or formula (3):

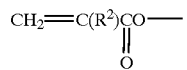

(2)

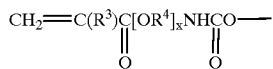

(3)

[wherein the symbols have the same meanings as in the above 2] and a polymerizable composition containing at least one organic solvent or further containing at least one inorganic oxide in a structure for constructing an electric double layer capacitor or disposing these on a support, polymerizing the polymerizable composition, and contacting the polymer obtained with an electrolytic solution to impregnate an electrolyte salt.

The present invention also provides the following production process of a solid polymer electrolyte.

[27] A process for producing a solid polymer electrolyte, comprising disposing at least one heat and/or active ray polymerizable compound having a poly- or oligo-carbonate group represented by formula (1'):

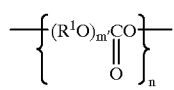

(1')

[wherein the symbols have the same meanings as in the above 10] and a polymerizable functional group represented by the following formula (3):

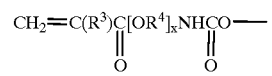

(3)

[wherein the symbols have the same meanings as in the above 2] and a polymerizable composition containing at least one electrolyte salt or further containing at least one organic solvent and/or at least one inorganic oxide on a support, and polymerizing the polymerizable composition.

[28] A process for producing a solid polymer electrolyte, comprising disposing at least one heat and/or active ray polymerizable compound having a poly- or oligo-carbonate group represented by formula (1'):

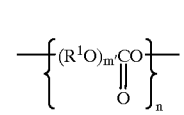

(1')

[wherein the symbols have the same meanings as in the above 10] and a polymerizable functional group represented by the following formula (3):

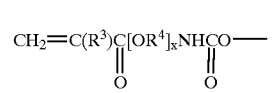

(3)

[wherein the symbols have the same meanings as in the above 2] and a polymerizable composition containing at least one organic solvent or further containing at least one inorganic oxide on a support, polymerizing the polymerizable composition, and contacting the polymer obtained with an electrolytic solution to impregnate an electrolyte salt.

The present invention also provides the following production process of a battery.

[29] A process for producing a battery, comprising placing at least one heat and/or active ray polymerizable compound having a poly- or oligo-carbonate group represented by formula (1'):

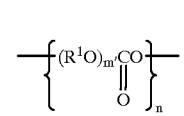

(1')

[wherein the symbols have the same meanings as in the above 10] and a polymerizable functional group represented by the following formula (3):

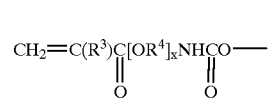

(3)

[wherein the symbols have the same meanings as in the above 2] and a polymerizable composition containing at least one electrolyte salt or further containing at least one organic solvent and/or at least one inorganic oxide in a structure for constructing a battery or disposing these on a support, and polymerizing the polymerizable composition.

[30] A process for producing a battery, comprising placing at least one heat and/or active ray polymerizable compound having a poly- or oligo-carbonate group represented by formula (1'):

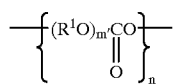
(1')

[wherein the symbols have the same meanings as in the above 10] and a polymerizable functional group represented by formula (3):

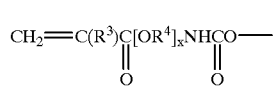
(3)

[wherein the symbols have the same meanings as in the above 2] and a polymerizable composition containing at least one organic solvent or further containing at least one inorganic oxide in a structure for constructing a battery or disposing these on a support, and contacting the polymer obtained with an electrolytic solution to impregnate an electrolyte salt.

The present invention also provides the following production process of an electric double layer capacitor.

[31] A process for producing an electric double layer capacitor, comprising placing at least one heat and/or active ray polymerizable compound having a poly- or oligo-carbonate group represented by formula (1'):

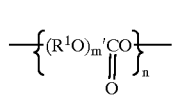
(1')

[wherein the symbols have the same meanings as in the above 10] and a polymerizable functional group represented by formula (3):

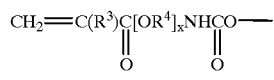
(3)

[wherein the symbols have the same meanings as in the above 1] and a polymerizable composition containing at least one electrolyte salt or further containing at least one organic solvent and/or at least one inorganic oxide in a structure for constructing an electric double layer capacitor or disposing these on a support, and polymerizing the polymerizable composition.

[32] A process for producing an electric double layer capacitor, comprising placing at least one heat and/or active ray polymerizable compound having a poly- or oligo-carbonate group represented by formula (1'):

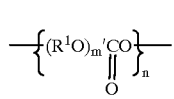
(1')

[wherein the symbols have the same meanings as in the above 10] and a polymerizable functional group represented by formula (3):

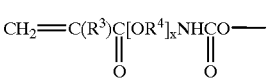
(3)

[wherein the symbols have the same meanings as in the above 2] and a polymerizable composition containing at least one organic solvent or further containing at least one inorganic oxide in a structure for constructing an electric double layer capacitor or disposing these on a support, polymerizing the polymerizable composition, and contacting the polymer obtained with an electrolytic solution to impregnate an electrolyte salt.

The present invention also provides the following polymerizable compounds.

[33] A polymerizable compound represented by formula (4):

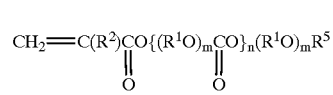
(4)

[wherein $R^1$ represents a chained, branched and/or cyclic divalent group having from 1 to 10 carbon atoms, which may contain a hetero atom, $R^2$ represents a hydrogen atom or an alkyl group having from 1 to 6 carbon atoms, $R^5$ represents a chained, branched and/or cyclic organic group having from 1 to 20 carbon atoms, which may contain a hetero atom, m represents an integer of from 3 to 10, and n represents an integer of from 2 to 1,000, provided that $R^1$, $R^2$, m and n which are present in plurality in the same molecule may be the same or different, respectively].

[34] A polymerizable compound represented by formula (5):

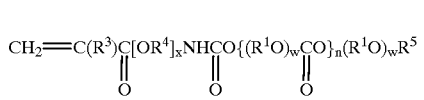
(5)

[wherein $R^1$ and $R^4$ each represents a chained, branched and/or cyclic divalent group having from 1 to 10 carbon atoms, which may contain a hetero atom, $R^3$ represents a hydrogen atom or an alkyl group having from 1 to 6 carbon atoms, $R^5$ represents a chained, branched and/or cyclic organic group having from 1 to 20 carbon atoms, which may contain a hetero atom, w represents an integer of from 1 to 10 carbon atoms, n represents an integer of from 2 to 1,000, and x represents 0 or an integer of from 1 to 10, provided that $R^1$, $R^3$, $R^4$, w, n and x which are present in plurality in the same molecule may be the same or different, respectively].

DETAILED DESCRIPTION OF THE INVENTION

Figure 1:
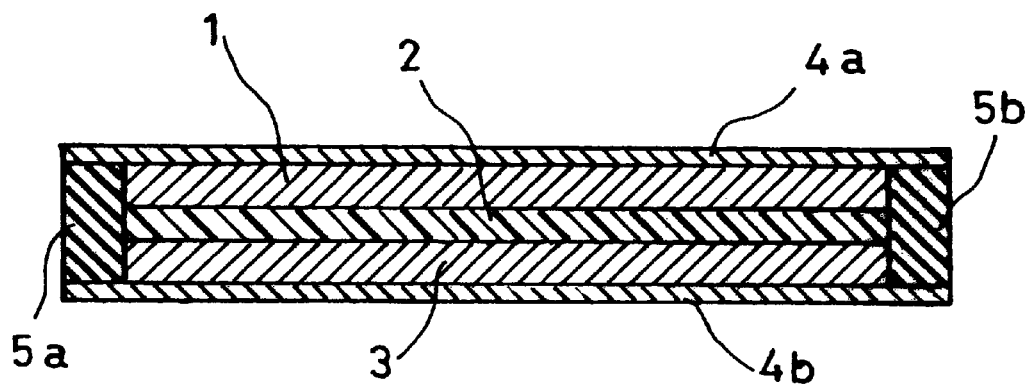
FIG. 1 is a schematic cross section of a thin battery produced in the Example as one example of the battery according to the present invention.

The present invention is described in detail below.
[Solid Polymer Electrolyte]

The solid polymer electrolyte of the present invention fundamentally comprises main constituent components, (a) a polymer compound and (b) an electrolyte salt, and may further contain (c) an organic solvent and (d) an inorganic oxide. Respective components are described in detail below.

(a) Polymer Compound (a-1) Structure

The polymer compound as a main constituent compound of the solid polymer electrolyte of the present invention is electronically non-conductive, can absorb and hold various organic polar solvent and contains a cross-linked and/or side chain group having a poly- or oligo-carbonate structure represented by the following formula (1):

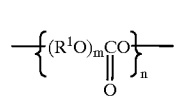

(1)

wherein $R^1$ represents a chained, branched and/or cyclic divalent group having from 1 to 10 carbon atoms, which may contain a hetero atom, m represents an integer of from 3 to 10, and n represents an integer of from 2 to 1,000.

If the carbon atom number of $R^1$ is too large, the carbonate group in the polymer compound is relatively reduced and disadvantageous, the dielectric constant lowers and the electrolyte salt difficultly dissociates. Furthermore, the polymer compound is intensified in the hydrophobic property and reduced in the compatibility with various polar solvents. The carbon atom number of $R^1$ is preferably from 1 to 4.

The repeating number n of the poly- or oligo-carbonate group represented by formula (1) in the polymer used in the solid polymer electrolyte of the present invention is from 2 to 1,000, preferably from 3 to 100, more preferably from 5 to 50.

It has been found that the value of m in formula (1) significantly effects the characteristics of the solid polymer electrolyte. That is, if m is 1 or 2, the content ratio of carbonate group in the cross-linked chain and/or side chain is too high in general, flexibility of the polymer is much impaired, the glass transition temperature becomes higher, and the ion conductivity lowers. On the contrary, if m exceeds 10, the ratio of carbonate group to polyether group in the polymer compound is relatively reduced and disadvantageous, the dielectric constant lowers and the electrolyte salt difficultly dissociates and, furthermore, there occurs a problem with regard to the durability of polyether chains. Accordingly, the preferred value of m is an integer from 3 to 10 in general, more preferably from 3 to 5.

The polymer of this type is preferably a polymer compound which contains a poly- and or oligo-carbonate group represented by formula (1) and is obtained by utilizing a polymerization reaction using a polymerizable functional group represented by the following formula (2) and/or formula (3):

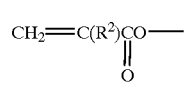

(2)

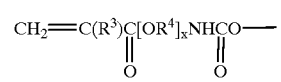

(3)

[wherein $R^2$ and $R^3$ each represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^2$, $R^3$, $R^4$ and x which are present in plurality in the same molecule may be the same or different, respectively] because working of the solid polymer electrolyte and compounding with an electrode used in various electrochemical elements are easy.

Specific examples of the polymer compound include:

(A) a polymer of a polymerizable compound which contains a poly- or oligo-carbonate group represented by the general formula (1) and a polymerizable functional group represented by the general formula (2) and/or formula (3); and (B) a reaction product of (a) a compound which contains a poly- or oligo-carbonate group represented by the general formula (1) and (b) a compound containing a group which reacts with the said compound (a) and a polymerizable functional group represented by the general formula (2) and/or formula (3).

Specific examples of the polymerizable compound of category (A) include the following compounds:

A polymerizable compound represented by formula (4):

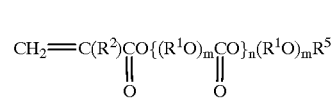

(4)

[wherein $R^1$ represents a chained, branched and/or cyclic divalent group having from 1 to 10 carbon atoms, which may contain a hetero atom, $R^2$ represents a hydrogen atom or an alkyl group having from 1 to 6 carbon atoms, $R^5$ represents a chained, branched and/or cyclic organic group having from 1 to 20 carbon atoms, which may contain a hetero atom, m represents an integer of from 3 to 10, and n represents an integer of from 2 to 1,000, provided that $R^1$, $R^2$, m and n which are present in plurality in the same molecule may be the same or different, respectively].

A polymerizable compound represented by formula (5a):

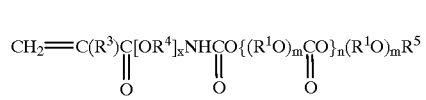

(5a)

[wherein $R^1$ and $R^4$ each represents a chained, branched and/or cyclic divalent group having from 1 to 10 carbon atoms, which may contain a hetero atom, $R^3$ represents a hydrogen atom or an alkyl group having from 1 to 6 carbon atoms, $R^5$ represents a chained, branched and/or cyclic organic group having from 1 to 20 carbon atoms, which may contain a hetero atom, m represents an integer of from 3 to 10 carbon atoms, n represents an integer of from 2 to 1,000, and x represents 0 or an integer of from 1 to 10, provided that $R^1$, $R^3$, $R^4$, m, n and x which are present in plurality in the same molecule may be the same or different, respectively].

In the case of category (B), compound (b) may be a compound which reacts with a compound (a) to form a group represented by the general formula (2) and/or (3). For example, when compound (a) is one having a hydroxyl group, compound (b) may be such a polymer in which the urethane group of the general formula (3) is replaced with isocyanate group.

The other examples of such compounds will be readily understood from the production process described below.

Further, (C) a mixture of a polymer of at least one compound which contains a polymerizable functional group and a poly- and or oligo-carbonate group represented by the general formula (1); and a polymer of at least one compound which contains a polymerizable functional group represented by the general formula (2) and/or (3) can be used. That is, the solid polymer electrolyte of the present invention may contain a polymer of at least one heat and/or active ray polymerizable compound having a polymerizable group represented by the general formula (2) and/or (3).

Furthermore, the present inventors have found that, when a polymerizable group represented by the general formula (3) in which a urethane group is connected with an acrylate group directly or through oxyalkylene is contained, good performance is attained even in the case that the repeating number of the oxyalkylene unit in the carbonate group (m in the formula (1)) is 1 or 2. Accordingly, a polymer compound which contains a poly- or oligo-carbonate group represented by formula (1'):

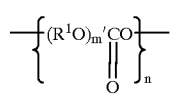

(1')

[wherein $R^1$ and n represent the same as in the general formula (1), m' represents 1 or 2, provided that $R^1$, m' and n which are present in plurality in the same molecule may be the same or different, respectively] and is obtained by utilizing a polymerization reaction using a polymerizable functional group represented by the general formula (3) can be used in the present invention.

Specific examples of the polymer compound include:
(A') a polymer of a polymerizable compound which contains a poly- or oligo-carbonate group represented by the general formula (1') and a polymerizable functional group represented by the general formula (3); and
(B') a reaction product of (a') a compound which contains a poly- or oligo-carbonate group represented by the general formula (1') and (b') a compound containing a group which reacts with the said compound (a') and a polymerizable functional group represented by the general formula (3).

Specific examples of the polymerizable compound of category (A') include the following compounds:

A polymerizable compound represented by formula (5b):

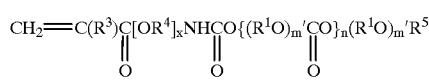

(5b)

[wherein the symbols represents the same as in the general formula (5a) except that m' is 1 or 2].

In case of the category (B'), compound (b') may be one which reacts with a compound mentioned above to form the group represented by formula (3), as is described with regard to the compound (b).

(a-2) Method for producing the polymerizable compound

The method of synthesizing the polymerizable compound having a group represented by the general formula (1) and a group represented by the general formula (2) is not particularly limited and the polymerizable compound can be easily obtained, for example, by reacting an acid chloride with a poly- or oligo-carbonate ol having a hydroxyl group at the terminal through the following process.

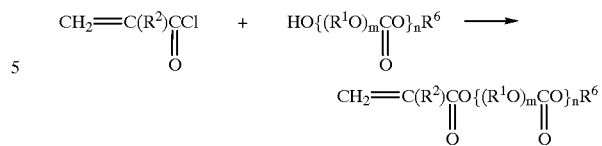

wherein $R^1$, m, n and $R^2$ have the same meanings as above.

The method of synthesizing the polymerizable compound having a group represented by formula (1) and a group represented by formula (3) is not particularly limited and the polymerizable compound can be easily obtained, for example, by reacting an isocyanate compound represented by the formula:

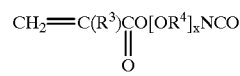

with a poly- or oligo-carbonate ol having a hydroxyl group at the terminal.

More specifically, the compound having one functional group represented by formula (3) can be easily obtained, for example, by reacting a methacryloyl isocyanate-base compound (hereinafter simply referred to as "a MI") or acryloyl isocyanate-base compound (hereinafter simply referred to as "an AI") with a monoalkyl poly- or oligo-carbonate ol at a molar ratio of 1:1 as shown in the reaction formula indicated below. Although the following examples are shown with regard to the general formula (1), it will be readily understood that the same will do with regard to the general formula (1').

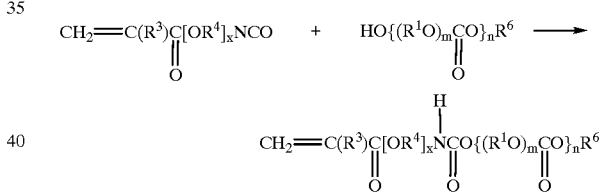

wherein $R^6$ represents an organic group having from 1 to 10 carbon atoms, and $R^1$, m, n, $R^3$, $R^4$ and x have the same meanings as above.

The compound having two functional groups represented by formula (3) can be easily obtained, for example, by reacting an MI or AI with a poly- or oligo-carbonate diol at a molar ratio of 2:1 as shown below:

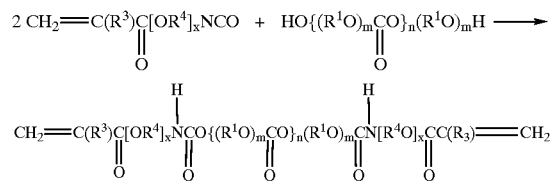

wherein $R^1$, m, b, n, $R^3$, $R^4$ and x have the same meanings as above.

The compound having three functional groups represented by formula (3) can be easily obtained, for example, by reacting an MI or AI with a poly- or oligo-carbonate triol at a molar ratio of 3:1.

Polymers obtained by polymerizing the compound having one functional group represented by formula (2) or (3) do not have a cross-linked structure and are deficient in the film strength, accordingly, when the polymer is formed into a thin film, short circuit occurs at a high probability. Accordingly, the polymer is preferably cross-linked by copolymerizing it with a polymerizable compound having two or more functional groups represented by formula (2) or (3) or preferably used in combination with a polymer obtained from a polymerizable compound having two or more functional groups represented by formula (2) or (3).

When the polymer is used as a thin film, in view of the film strength thereof, the number of functional groups represented by formula (2) or (3) contained in one molecule is preferably 3 or more.

The polymer compound obtained by polymerizing a compound having a polymerizable functional group represented by formula (3) contains a urethane group and is advantageous in that the dielectric constant is high and the solid polymer electrolyte obtained has high ion conductivity. Further, the compound having a polymerizable functional group represented by formula (3) has good polymerizability and the thin film formed has a large film strength, as a result, the amount of electrolytic solution contained is advantageously increased.

The polymer compound preferred as a constituent component of the solid polymer electrolyte of the present invention may be a homopolymer of the above-described polymerizable compound, a copolymer of two or more compounds belonging to the same category, or a copolymer of at least one of the above-described polymerizable compounds with another polymerizable compound.

The other polymerizable compound which can be copolymerized with the above-described polymerizable compound is not particularly limited but examples thereof include (meth)acrylic acid alkyl esters such as methyl methacrylate and n-butyl acrylate; various urethane (meth) acrylates; acrylic acid esters and/or urethane (meth)acrylates having an oxyalkylene and/or oxyfluorocarbon chain; (meth)acrylic acid fluorinated alkyl esters; (meth) acrylamide-base compounds such as acrylamide, methacrylamide, N,N-dimethylacrylamide, N,N-dimethylmethacrylamide, vinylene carbonate, (meth) acryloyl carbonate, N-vinylpyrrolidone, acryloylmorpholine, methacryloylmorpholine and N,N-dimethylaminopropyl-(meth)acrylamide; styrene-base compounds such as styrene and a-methylstyrene; N-vinylamide-base compounds such as N-vinylacetamide and N-vinylformamide; and alkyl vinyl ethers such as ethyl vinyl ether.

Among these, preferred are (meth)acrylic acid esters, urethane (meth)acrylates, and (meth)acrylic acid esters and/or urethane (meth)acrylates having an oxyalkylene and/or oxyfluorocarbon chain, and more preferred in view of polymerizability is urethane (meth)acrylate.

The polymer compound belonging to the above category (B) includes the above-exemplified compounds and besides them can be also obtained by reacting (b-1) at least one compound containing a polymerizable group represented by the general formula (2) and/or the general formula (3) and (b-2) at least one compound containing a poly- or oligocarbonate group represented by the general formula (1) and a functional group which reacts with the said polymerizable group. Examples of the functional group contained in the compound (b-2) which reacts with the polymerizable group include vinyl group and the other unsaturated bonds and epoxy group and the like. The reaction of the compounds (b-1) and (b-2) may be such a reaction that proceeds between (b-2) and a functional group contained in the compound (b-1) other than the above-mentioned polymerizable group. The polymer compound belonging to the above category (B') can be obtained in the same way except that the reaction is effected between at least one compound containing a polymerizable group represented by the general formula (3) and at least one compound containing a poly- or oligocarbonate group represented by the general formula (1').

As stated in the above category (C), the polymer compound for use in the solid polymer electrolyte of the present invention may be a mixture of polymers, said mixture comprising a polymer of at least one compound which contains the poly or oligo-ether/carbonate structure represented by the general forumula (1) and a polymer of at least one compound which contains the polymerizable group represented by the general formula (2) and/or the general formula (3).

Further, the polymer compound for use in the solid polymer electrolyte of the present invention may be a mixture of polymers, said mixture comprising a polymer obtained from at least one of the above-described polymerizable compounds and/or a copolymer using the above-described polymerizable compound as a copolymerization component, and another polymer compound. Examples of the other polymer compound to be mixed include polymers such as polyethylene oxide, polypropylene oxide, polyacrylonitrile, polybutadiene, polymethacrylic (or acrylic) acid esters, polystyrene, polyphosphazenes, polysiloxane, polysilane, polyvinylidene fluoride and polytetrafluoroethylene.

The amount of the constituent unit originated from the polymer having a poly- and/or oligo-ether carbonate group represented by formula (1) varies depending on whether the above-described polymerizable compound is homopolymerized, copolymerized with another copolymerization component or mixed with another polymer compound or on the kind thereof and cannot be specified at large, however, in view of the ion conductivity, film strength, heat resistance and current characteristics in the case of use in a solid polymer electrolyte, the amount thereof is preferably 50 wt % or more, more preferably 70 wt % or more, based on the entire amount of the polymer component.

The above-described polymerizable compound may be polymerized by a general method using the polymerizability of the acryloyl group or methacryloyl group as the functional group. More specifically, the polymerizable compound alone or a mixture of the polymerizable compound and another polymerizable compound which can be copolymerized with the above-described polymerizable compound may be subjected to radical polymerization, cationic polymerization or anionic polymerization using a radical polymerization catalyst such as azobisisobutyronitrile or benzoyl peroxide, a cationic polymerization catalyst such as protonic acid (e.g., $CF_3COOH$) or Lewis acid (e.g., $BF_3$, $AlCl_3$), or an anionic polymerization catalyst such as butyl lithium, sodium naphthalene or lithium alkoxide. The polymerizable compound or polymerizable mixture may also be polymerized after forming it into a shape such as film.

(b) Electrolyte Salt

The kind of the electrolyte salt for use in the present invention is not particularly limited and an electrolyte salt containing an ion intended to be a charge carrier may be used, however, the electrolyte salt preferably has a large dissociation constant in the solid polymer electrolyte. Preferred examples thereof include alkali metal salts such as $LiCF_3SO_3$, $LiN(CF_3SO_2)_2$, $LiN(CF_3CF_2SO_2)_2$, $LiPF_6$, $LiClO_4$, $LiI$, $LiBF_4$, $LiSCN$, $LiAsF_6$, $NaCF_3SO_3$, $NaPF_6$, $NaClO_4$, $NaI$, $NaBF_4$, $NaAsF_6$, $KCF_3SO_3$, $KPF_6$ and $KI$, quaternary ammonium salts such as $(CH_3)_4NBF_4$, quaternary phosphonium salts such as $(CH_3)_4PBF_4$, transition metal salts such as $AgClO_4$, and protonic acids such as hydrochloric acid, perchloric acid and borofluoric acid.

The electrolyte salt in the solid polymer electrolyte of the present invention may be compounded on use and the compounding ratio thereof is preferably from 0.1 to 50 wt %, more preferably from 1 to 30 wt %, based on the weight of the polymer. If the electrolyte salt compounded is present at a ratio of 50 wt % or more, the ion is greatly inhibited from moving, whereas if the ratio is less than 0.1 wt %, the absolute amount of ion is deficient and the ion conductivity is reduced.

(c) Organic Solvent

An organic solvent is preferably added to the solid polymer electrolyte of the present invention because the ion conductivity of the solid polymer electrolyte is further improved. The organic solvent which can be used is suitably a compound having good compatibility with the compound having an organic group represented by formula (1), having a large dielectric constant, having a boiling point of 60° C. or higher and being electrochemically stable over a wide range.

Examples of the solvent include ethers such as 1,2-dimethoxyethane, 2-methyltetrahydrofuran, crown ether, triethylene glycol methyl ether and tetraethylene glycol dimethyl ether, carbonates such as ethylene carbonate, propylene carbonate, dimethyl carbonate, diethyl carbonate and ethyl methyl carbonate, aromatic nitriles such as benzonitrile and tolunitrile, sulfur compounds such as dimethylsulfoxide and sulfolane, dimethylformamide, N-methylpyrrolidone, N-vinyl-pyrrolidone, and phosphoric acid esters. Among these, ethers and carbonates are preferred, and carbonates are more preferred.

As the amount of the organic solvent added is larger, the ion conductivity of the solid polymer electrolyte is more improved. Accordingly, the addition amount is in general preferably increased, however, if the addition amount is too large, the mechanical strength of the solid polymer electrolyte decreases in turn. The addition amount is preferably from 2 to 15 times, more preferably from 3 to 10 times, the weight of the polymer used in the solid polymer electrolyte of the present invention.

(d) Inorganic Oxide

The solid polymer electrolyte of the present invention preferably contains various inorganic oxides. By adding an inorganic oxide, not only the strength and the uniformity in the film thickness are improved but also fine vacancy is generated between the inorganic oxide and the polymer and when the electrolyte is dipped in an electrolytic solution, free electrolytic solution can be dispersed into the solid polymer electrolyte through the vacancy, as a result, the ion conductivity and ion mobility can be elevated without impairing the effect of improving the strength. Further, by adding an inorganic oxide, the viscosity of the polymerizable composition increases and even when the compatibility between the polymer and the solvent is insufficient, these can be effectively inhibited from separation.

The inorganic oxide used is selected from those which are electronically non-conductive and electrochemically stable. Those having ion conductivity are more preferred. Specific examples thereof include ion conductive or electrically non-conductive ceramic fine particles such as $\alpha$-alumina, $\beta$-alumina, $\gamma$-alumina, silica, titania, magnesia and hydrotalcite.

For the purpose of increasing the amount of the holding electrolytic solution in the solid polymer electrolyte and intensifying the ion conductivity and mobility, the inorganic oxide preferably has a specific surface area as large as possible and by BET method, it is 10 $m^2/g$ or more, more preferably 50 $m^2/g$ or more.

The inorganic oxide is not particularly limited on the crystal grain size as far as it can be mixed with the polymerizable composition but the size is preferably from 0.001 to 10 $\mu m$, more preferably from 0.01 to 1 $\mu m$.

The shape may be selected from various forms such as spherical, egg, cubic, rectangular parallelopiped, cylindrical and bar forms.

If the amount of inorganic oxide added is too large, there arises a problem that the strength or ion conductivity of the solid polymer electrolyte lowers or a film is difficult to form. Accordingly, the amount of inorganic oxide added is preferably 50 wt % or less, more preferably from 0.1 to 30 wt %, based on the solid polymer electrolyte.

[Production process of Solid Polymer Electrolyte]

The solid polymer electrolyte of the present invention may be produced by a method of forming a polymer obtained from at least one of the above-described polymerizable compounds or a copolymer containing the polymerizable compound as a copolymerization component, for example, into a film, and polymerizing and then contacting it with an electrolyte salt dissolved in an organic solvent, or by a method of preparing a polymerizable composition comprising the above-described polymerizable compound and other components, forming the composition, for example, into a film and then polymerizing the composition.

To speak more specifically about the latter method, a polymerizable composition is prepared by mixing at least one of the above-described polymerizable compounds and at least one electrolyte salt such as an alkali metal salt, a quaternary ammonium salt, a quaternary phosphonium salt or a transition metal salt and, if desired, further adding thereto another polymerizable compound, a plasticizer, an organic solvent and/or an inorganic oxide, and the resulting composition is formed into a film or the like and then polymerized in the presence or absence of the above-described catalyst under heating and/or irradiation of an active ray to obtain the solid polymer electrolyte of the present invention. According to this method, the degree of freedom expands in view of working and this is a great merit in the application.

In the case of using a solvent at the polymerization, although it may vary depending on the kind of the polymerizable compound or the presence or absence of the polymer catalyst, any solvent may be used as far as it does not inhibit the polymerization, and for example, tetrahydrofuran (THF), acetonitrile, toluene and the like may be used.

The polymerization temperature varies depending on the kind of the polymerizable compound, however, it suffices if the polymerization can start. The polymerization may be performed usually at from 0 to 200° C.

In the case where the polymerization is effected by the irradiation of an active ray, although it may depend on the kind of the polymerizable compound, the polymerization may be performed using an initiator such as benzyl methyl ketal or benzophenone, under the irradiation of ultraviolet ray of several mW or more or of $\gamma$-ray or an electron beam.

In the case where the solid polymer electrolyte of the present invention is used as a thin film, a composite film with another porous film may be formed so as to increase the film strength, however, the film compounded must be appropriately selected because depending on the kind or amount of the film compounded, the conductivity may be reduced or the stability may be deteriorated. Examples of the film which can be used include a porous polyolefin sheet such as network polyolefin sheet, e.g., polypropylene-made non-woven fabric or polyethylene-made net; a polyolefin-made microporous film such as Cellgard (trade name); and a nylon non-woven fabric, with the porous polyolefin film being preferred. The porosity may be sufficient if it is approximately from 10 to 95%, however, the porosity is preferably as large as possible if the strength permits and the porosity is preferably from 40 to 95%.

The compounding method is not particularly limited, however, for example, a method of impregnating a polymerizable composition obtained by adding and mixing at least one of the above-described polymerizable compounds or additionally at least one electrolyte salt and if desired, other components, into a porous polymer film and polymerizing the (meth)acryloyl-base compound, may be used and according to this method, the compounding can be uniformly performed and the film thickness can be easily controlled.

[Battery and Production Process Thereof]

FIG. 1 is a schematic cross section showing one example of a thin film solid secondary battery as a battery of the present invention. In the figure, 1 is a positive electrode, 2 is a solid polymer electrolyte, 3 is a negative electrode, 4a and 4b are collector bodies and 5a and 5b are an insulating resin sealant.

In the construction of the battery of the present invention, an electrode active material (positive electrode active material) having a high oxidation-reduction potential, such as a metal oxide, a metal sulfide, an electroconductive polymer or a carbon material, is preferably used as the positive electrode 1 so as to obtain a battery having a high voltage and a high capacity. Among these electrode active materials, in view of high packing density and increased volume capacity density, metal oxides such as cobalt oxide, manganese oxide, vanadium oxide, nickel oxide and molybdenum oxide, and metal sulfides such as molybdenum sulfide, titanium sulfide and vanadium sulfide are preferred, and in view of high capacity and high voltage, manganese oxide, nickel oxide and cobalt oxide are more preferred.

In this case, the method for producing the metal oxide or metal sulfide is not particularly limited and, for example, the electrolytic method or heating method in general as described in *Denki Kagaku* (*Electrochemistry*), Vol. 22, page 574 (1954) may be used. In using this as the electroactive material in a lithium battery, the lithium element in the form, for example, of $Li_xCoO_2$ or $Li_xMnO_2$ is preferably intercalated (compounded) into the metal oxide or metal sulfide at the production of the battery. The method for intercalating the lithium element is not particularly limited and for example, a method of electrochemically intercalating the lithium ion or a method of mixing a salt of $Li_2CO_3$ with a metal oxide and heating the mixture described in U.S. Pat. No. 4,357,215 may be used.

An electroconductive polymer is preferred in the point that it is flexible and easily formed into a thin film. Examples of the electroconductive polymer include polyaniline, polyacetylene and derivatives thereof, polyparaphenylene and derivatives thereof, polypyrrole and derivatives thereof, polythienylene and derivatives thereof, polypyridinediyl and derivatives thereof, polyisothianaphthenylene and derivatives thereof, polyfurylene and derivatives thereof, polyselenophene and derivatives thereof, and polyarylene vinylene and derivatives thereof such as polyparaphenylene vinylene, polythienylene vinylene, polyfurylene vinylene, polynaphthenylene vinylene, polyselenophene vinylene and polypyridinediyl vinylene. Among these, polymers of an aniline derivative soluble in an organic solvent are preferred. The electroconductive polymer used as an electroactive material in the battery or electrode is produced by a chemical or electrochemical method described later or according to other known methods.

Examples of the carbon material include natural graphite, artificial graphite, graphite grown by vapor phase method, petroleum coke, coal coke, fluoride graphite, pitch-base carbon and polyacene.

As the negative electrode active material used as the negative electrode 3 in the battery of the present invention, those having a low oxidation-reduction potential with the carrier being an alkali metal ion, such as an alkali metal, an alkali metal alloy, a carbon material, a metal oxide or an electroconductive polymer compound, are preferred because the battery obtained can have high voltage and high capacity. Among these negative electrode active materials, lithium metals and lithium alloys such as lithium/aluminum alloy, lithium/lead alloy and lithium/antimony alloy, are particularly preferred because these have a lowest oxidation-reduction potential and can be formed into a thin film. Carbon materials are also particularly preferred because they come to have a low oxidation-reduction potential after occluding lithium ion and moreover, these are stable and safe. Examples of the material capable of occluding and releasing lithium ion include natural graphite, artificial graphite, graphite grown by vapor phase method, petroleum coke, coal coke, pitch-base carbon, polyacene and furalenes such as $C_{60}$ and $C_{70}$.

In the case of a battery using the above-described negative electrode active material and also an alkali metal ion as the carrier, the electrolyte salt used in the solid polymer electrolyte is an alkali metal salt. Examples of the alkali metal salt include $LiCF_3SO_3$, $LiPF_6$, $LiClO_4$, $LiBF_4$, $LiSCN$, $LiAsF_6$, $LiN(CF_3SO_2)_2$, $LiN(CF_3 CF_2SO_2)_2$, $NaCF_3SO_3$, $LiI$, $NaPF_6$, $NaClO_4$, $NaI$, $NaBF_4$, $NaAsF_6$, $KCF_3SO_3$, $KPF_6$ and $KI$.

One example of the production process of the electrode or battery of the present invention is described below.

A positive electrode and a negative electrode are placed in a structure for constructing a battery so as not to come into contact with each other or disposed on a support. For example, the positive electrode and the negative electrode are laminated through a spacer having an appropriate thickness at the edges of the electrodes or through a polymer solid electrolyte film previously prepared, and placed in the above-described structure. Then, a polymerizable composition obtained by adding and mixing at least one polymerizable compound or additionally at least one electrolyte salt and if desired, another polymerizable compound and/or a plasticizer and/or a solvent and/or an inorganic oxide is injected between the positive electrode and the negative electrode. Thereafter, the composition is polymerized, for example, under heating and/or irradiation of an active ray and thereby, or after the polymerization, if desired, by further sealing the structure with an insulating resin such as polyolefin resin or an epoxy resin, a battery having good contact between the electrode and the electrolyte can be obtained.

Other than this process, a battery may also be produced by laminating a positive electrode and a negative electrode through a polymer obtained by polymerizing a polymerizable composition prepared by adding and mixing at least one polymerizable compound, a solvent or additionally another polymerizable compound and/or a plasticizer and/or an inorganic oxide, and transferring a part of the electrolyte salt to the polymer from an electrolytic solution previously impregnated into the electrodes.

The structure for constructing this battery or the support may be a metal such as SUS, a resin such as polypropylene or polyimide, or a ceramic material such as electroconductive or insulating glass, however, the structure is not limited particularly to these materials. The shape thereof may be any of cylinder, box, sheet and the like.

In producing a roll-type battery, method where the positive electrode and the negative electrode are laminated through a solid polymer electrolyte film previously prepared, the laminate is rolled and inserted into a structure for constructing a battery, and then the above-described polymerizable composition is injected therein and polymerized, may also be used.

[Electric Double Layer Capacitor and Production Process Thereof]

The electric double layer capacitor of the present invention is described below.

According to the present invention, an electric double layer capacitor having high output voltage, large takeout current and excellent workability and reliability can be provided by using the above-described solid polymer electrolyte.

Figure 2:
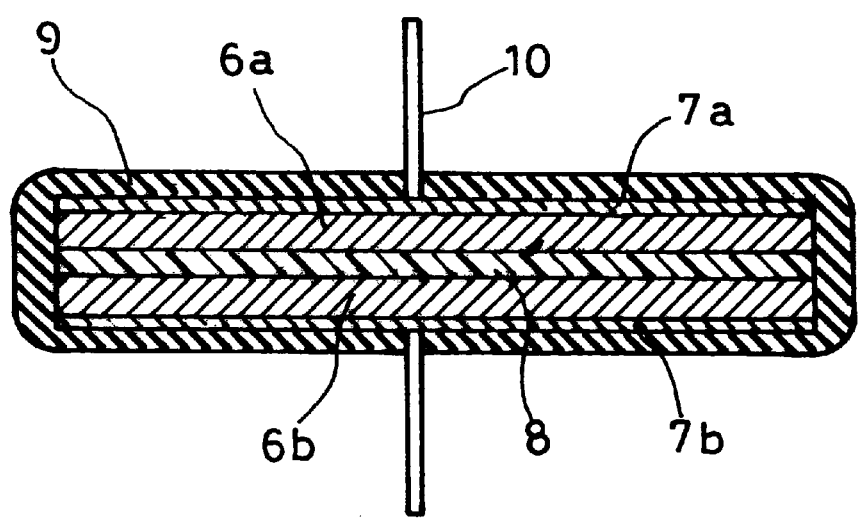
FIG. 2 is a schematic cross section of an electric double layer capacitor produced in the Example according to the present invention.

FIG. 2 shows a schematic cross section of one example of the electric double layer capacitor of the present invention. This example shows a thin-type cell having a size of 1 cm×1 cm and a thickness of about 0.5 mm, where 7a and 7b are collector bodies, a pair of polarizable electrodes 6a and 6b are disposed inside of the collector bodies, and a solid polymer electrolyte film 8 is disposed therebetween. The numeral 9 is an insulating resin sealant and 10 is a lead wire.

The material used for the collector body 7 is an electronically conductive and electrochemically anticorrosive, and preferably has a specific surface area as large as possible. Examples thereof include various metals and a sintered body thereof, electronic conductive polymers, and carbon sheet.

The polarizable electrode 6 may be an electrode comprising a polarizable material such as a carbon material usually used in an electric double layer capacitor. The carbon material as the polarizable material is not particularly restricted as long as the specific surface area is large, however, carbon materials having a larger specific surface area are preferred because the electric double layer can have a larger capacity. Examples thereof include carbon blacks such as furnace black, thermal black (including acetylene black) and channel black, activated carbons such as coconut husk carbon, natural graphite, artificial graphite, so-called pyrolytic graphite obtained by the vapor phase process, polyacene, $C_{60}$ and $C_{70}$.

In the case of the electric double layer capacitor of the present invention, the kind of the electrolyte salt used in the compounding is not particularly restricted and a compound containing an ion intended to be a charge carrier may be used, however, the compound preferably contains an ion having a large dissociation constant in the solid polymer electrolyte and capable of easily forming an electric double layer with the polarizable electrode. Examples of such a compound include quaternary ammonium salts such as $(CH_3)_4NBF_4$ and $(CH_3CH_2)_4NClO_4$, pyridinium salts, transition metal salts such as $AgClO_4$, quaternary phosphonium salts such as $(CH_3)_4PBF_4$, alkali metal salts such as $LiCF_3SO_3$, $LiPF_6$, $LiClO_4$, $LiI$, $LiBF_4$, $LiSCN$, $LiAsF_6$, $LiN(CF_3SO_2)_2$, $LiN(CF_3 CF_2SO_2)_2$, $NaCF_3SO_3$, $NaPF_6$, $NaClO_4$, $NaI$, $NaBF_4$, $NaAsF_6$, $KCF_3SO_3$, $KPF_6$ and $KI$, organic acids and salts thereof such as p-toluenesulfonic acid, and inorganic acids such as hydrochloric acid and sulfuric acid. Among these, quaternary ammonium salts, pyridinium salts, quaternary phosphonium salts and alkali metal salts are preferred from the standpoint that high output voltage can be obtained and their dissociation constant is large. Among quaternary ammonium salts, those having different substituents on the nitrogen of the ammonium ion, such as $(CH_3CH_2)$ $(CH_3CH_2CH_2CH_2)_3NBF_4$, are preferred because of their high solubility or large dissociation constant in the solid polymer electrolyte.

One example of the production process of the electric double layer capacitor of the present invention is described below.

Two sheets of polarizable electrodes are placed in a structure for constructing a capacitor so as not to come into contact with each other or disposed on a support. For example, the polarizable electrodes are laminated through a spacer having an appropriate thickness at the edges of the electrodes or through a polymer solid electrolyte film previously prepared, and placed in the above-described structure. Then, a polymerizable composition obtained by adding and mixing at least one polymerizable compound or additionally at least one electrolyte salt and if desired, another polymerizable compound and/or a plasticizer and/or a solvent and/or an inorganic oxide is injected therein and polymerized, and thereby, or after the polymerization, if desired, by further sealing the structure with an insulating resin such as polyolefin resin or an epoxy resin, an electric double layer capacitor having good contact between the electrode and the electrolyte can be obtained. According to this process, particularly a thin electric double layer capacitor can be produced.

Other than this process, an electric double layer capacitor may also be produced by laminating two sheets of polarizable electrodes through a polymer obtained by polymerizing a polymerizable composition prepared by adding and mixing at least one polymerizable compound, a solvent or additionally another polymerizable compound and/or a plasticizer and/or an inorganic oxide, and transferring a part of the electrolyte salt to the polymer from an electrolytic solution previously impregnated into the polarizable electrodes.

The structure for constructing this capacitor or the support may be a metal such as SUS, a resin such as polypropylene or polyimide, or a ceramic material such as electroconductive or insulating glass, however, the structure is not limited particularly to these materials. The shape thereof may be any of cylinder, box, sheet and the like.

With respect to the shape of the electric double layer capacitor, in addition to the sheet form as shown in FIG. 2, a coin-type capacitor or a cylindrical capacitor produced by rolling a sheet-like laminate of polarizable electrodes and a solid polymer electrolyte into a cylinder form, placed in a cylindrical structure for constructing a capacitor, and sealing the structure, may also be formed.

In producing a roll-type capacitor, a method where the polarizable electrodes are laminated through a solid polymer electrolyte film previously prepared, the laminate is rolled and inserted into a structure for constructing a capacitor, and then the above-described polymerizable composition is injected therein and polymerized, may also be used.

BEST MODE FOR CARRYING OUT THE INVENTION

The present invention is described in greater detail below by referring to representative Examples. These are Examples only for the illustration and the present invention is by no means limited thereto.

EXAMPLE 1

Synthesis of Compounds 1, 2 and 3

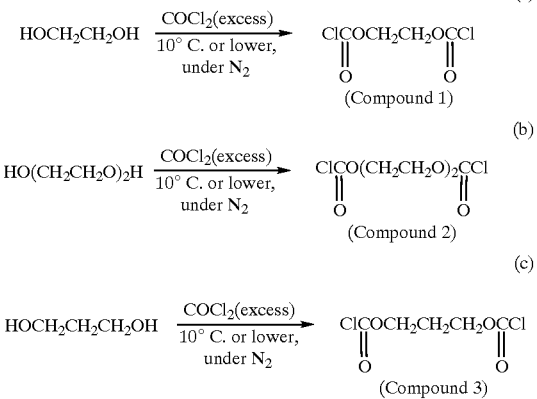

According to the formula (a), (b) or (c) above, excess phosgene gas was blown into alkylene glycol the kind of which was variously changed, at 10° C. or lower under nitrogen in an ordinary manner and reacted for about 5 hours to synthesize Compound 1, Compound 2 or Compound 3 as a bischloroformate form of respective alkylene glycols. The compounds were identified by GC-MS.

EXAMPLE 2

Oligomerization of Compounds 1, 2 and 3 (Synthesis of Compounds 4, 5 and 6)

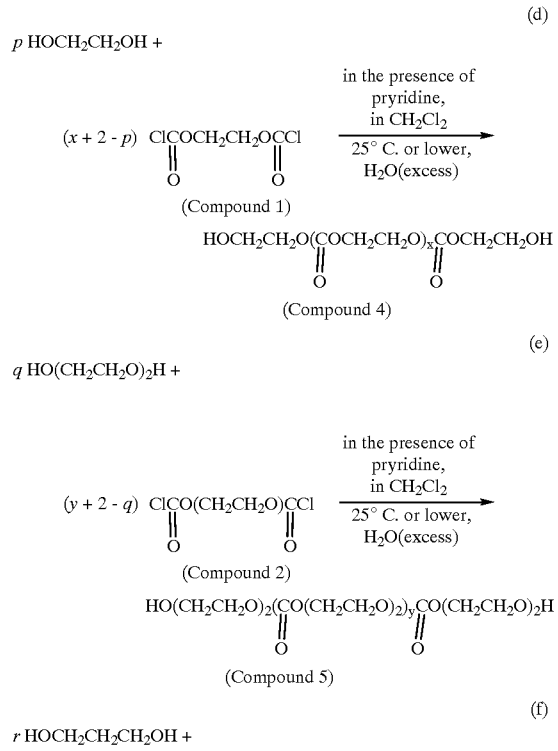

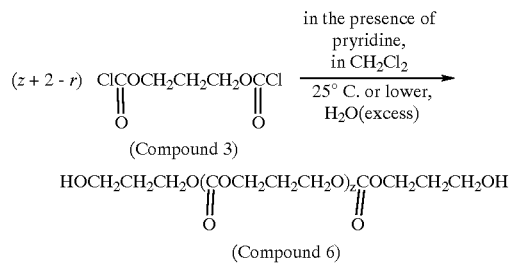

According to the formula (d), (e) or (f), the bischloroformate form of various alkylene glycols (Compound 1, 2 or 3) and an alkylene glycol the kind of which was variously changed, were reacted at 25° C. or lower for about 6 hours in the presence of pyridine in dichloromethane. Thereafter, excess water was added to hydroxylate the residual chloroformate terminal, thereby synthesizing an oligocarbonate having a hydroxyl group at both terminals (Compound 4, Compound 5 or Compound 6).

The weight average molecular weight (Mw) and the average repeating number x, y or z of each oligocarbonate, determined by the GPC analysis, are shown below.

Compound 4 Mw: up to about 800 x: up to about 8
Compound 5 Mw: up to about 1,500 y: up to about 10
Compound 6 Mw: up to about 1,200 z: up to about 10

EXAMPLE 3

Synthesis of Compound 7

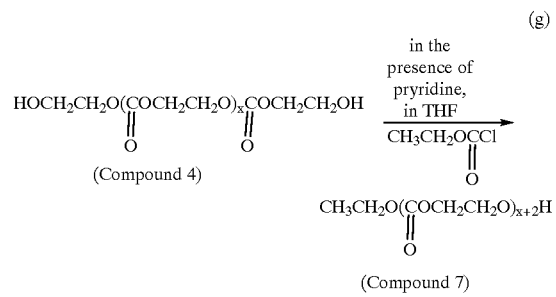

To an anhydrous THF solution of the carbonate oligomer (Compound 4) synthesized in Example 2 according to formula (g), an equimolar amount of ethyl chloroformate was gradually added dropwise at 25° C. or lower in the presence of pyridine by a usual method, and the resulting mixed solution was reacted for about 6 hours to synthesize an oligocarbonate with one terminal being hydroxylated (Compound 7).

EXAMPLE 4

Synthesis of Polymerizable Compound 8

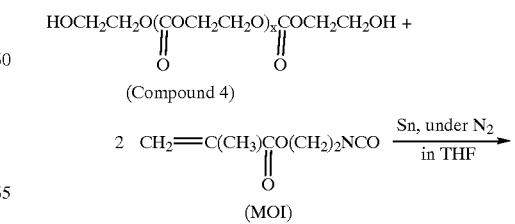

-continued

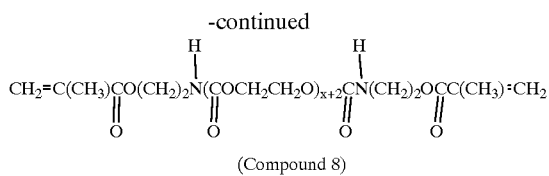

(Compound 8)

Compound 4 (average molecular weight: 800) (40.0 g) and MOI (methacryloyloxyethyl isocyanate) (15.5 g) were dissolved in 200 ml of thoroughly purified THF in a nitrogen atmosphere, and thereto 0.44 g of dibutyltin dilaurate was added. Thereafter, the resulting mixed solution was reacted at 25° C. for about 15 hours, as a result, a colorless product was obtained. From the results of $^1$H-NMR, IR and elemental analysis thereof, it was found that Compound 4 and MOI were reacted at 1:2, the isocyanate group of MOI disappeared, a urethane bond was generated and Compound 8 was produced.

EXAMPLE 5
Synthesis of Polymerizable Compound 9

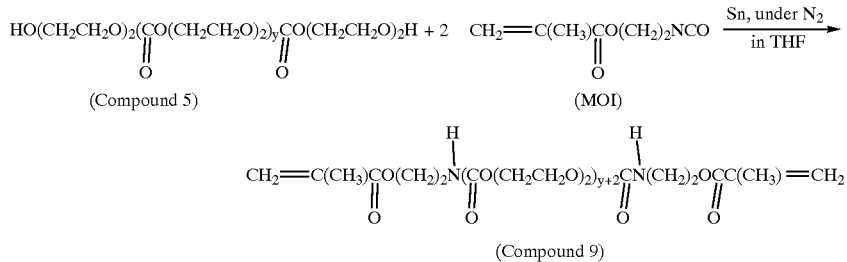

Compound 5 (average molecular weight: 1,500) (75.0 g) and MOI (15.5 g) were dissolved in thoroughly purified THF (200 ml) in a nitrogen atmosphere, and thereto dibutyltin dilaurate (0.44 g) was added. Thereafter, the resulting mixed solution was reacted at 25° C. for about 15 hours, as a result, a colorless product was obtained. From the results of $^1$H-NMR, IR and elemental analysis thereof, it was found that Compound 5 and MOI were reacted at 1:2, the isocyanate group of MOI disappeared, a urethane bond was generated and Compound 9 was produced.

EXAMPLE 6
Synthesis of Polymerizable Compound 10

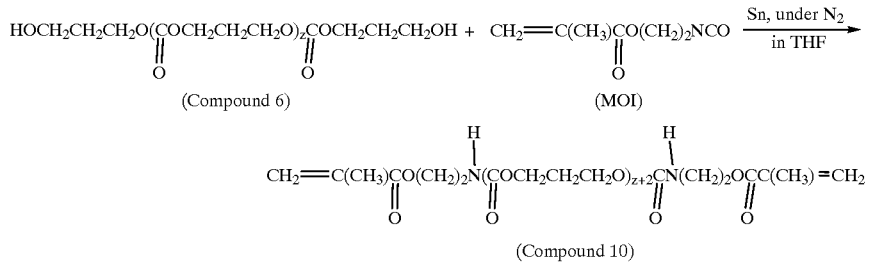

Compound 6 (average molecular weight: 1,200) (60.0 g) and MOI (15.5 g) were dissolved in thoroughly purified THF (200 ml) in a nitrogen atmosphere, and thereto dibutyltin dilaurate (0.44 g) was added. Thereafter, the resulting mixed solution was reacted at 25° C. for about 15 hours, as a result, a colorless product was obtained. From the results of $^1$H-NMR, IR and elemental analysis thereof, it was found that Compound 6 and MOI were reacted at 1:2, the isocyanate group of MOI disappeared, a urethane bond was generated and Compound 10 was produced.

EXAMPLE 7

Synthesis of Polymerizable Compound 11

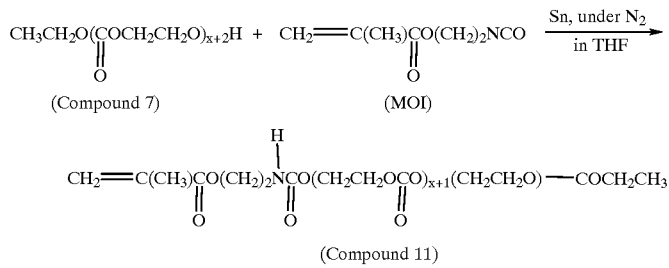

(Compound 11)

Compound 7 (average molecular weight: 900) (90.0 g) and MOI (15.5 g) were dissolved in thoroughly purified THF (200 ml) in a nitrogen atmosphere, and thereto dibutyltin dilaurate (0.44 g) was added. Thereafter, the resulting mixed solution was reacted at 25° C. for about 15 hours, as a result, a colorless product was obtained. From the results of $^1$H-NMR, IR and elemental analysis thereof, it was found that Compound 7 and MOI were reacted at 1:1, the isocyanate group of MOI disappeared, a urethane bond was generated and Compound 11 was produced.

EXAMPLE 8
Production of Solid Polymer Electrolyte Film (Compound 8):

Compound 8 (2.0 g), ethylene carbonate (EC) (1.8 g), ethyl methyl carbonate (EMC) (4.2 g), LiPF$_6$ (battery grade produced by Hashimoto Kasei) (0.60 g) and 2,4,6-trimethylbenzoyl-diphenylphosphine oxide ("Lucirin TPO", trade name, produced by BASF) (0.010 g) were thoroughly mixed in an argon atmosphere to obtain a photopolymerizable composition. This composition had a moisture content (by Karl Fischer's method) of 30 ppm. The photopolymerizable composition obtained was applied on a PET film in an argon atmosphere and then irradiated with a chemical fluorescent lamp (FL20S.BL manufactured by Sankyo Denki) for 10 minutes. As a result, a polymer (Compound 8) film impregnated with an EC/EMC-base electrolytic solution was obtained as a self-standing film having a thickness of about 30 μm. The resulting film had an ion conductivity at 25° C. or −20° C. measured by the impedance method, of 2.5×10$^{-3}$ S/cm or 0.6×10$^{-3}$ S/cm, respectively.

EXAMPLE 9
Production of Solid Polymer Electrolyte Film (Compound 9)

A polymer (Compound 9) film impregnated with an EC/EMC-base electrolytic solution was obtained as a self-standing film having a thickness of about 30 μm in the same manner as in Example 8 except for using Compound 9 (2.0 g) in place of Compound 8. The resulting film had an ion conductivity at 25° C. or −20° C. measured by the impedance method, of 2.2×10$^{-3}$ S/cm or 0.5×10$^{-3}$ S/cm, respectively.

EXAMPLE 10
Production of Solid Polymer Electrolyte Film (Compound 10)

A polymer (Compound 10) film impregnated with an EC/EMC-base electrolytic solution was obtained as a self-standing film having a thickness of about 30 μm in the same manner as in Example 8 except for using Compound 10 (2.0 g) in place of Compound 8. The resulting film had an ion conductivity at 25° C. or −20° C. measured by the impedance method, of 1.8×10$^{-3}$ S/cm or 0.5×10$^{-3}$ S/cm, respectively.

EXAMPLE 11
Production of Solid Polymer Electrolyte Film (Compound 9+Compound 11)

A copolymer (Compound 9+Compound 11) film impregnated with an EC/EMC-base electrolytic solution was obtained as a self-standing film having a thickness of about 30 μm in the same manner as in Example 8 except for using a mixture of Compound 9 (1.0 g) and Compound 11 (1.0 g) in place of Compound 8. The resulting film had an ion conductivity at 25° C. or −20° C. measured by the impedance method, of 2.8×10$^{-3}$ S/cm or 0.9×10$^{-3}$ S/cm, respectively.

EXAMPLE 12
Production of Solid Polymer Electrolyte Composite Film (Compound 8+Compound 10)

Compound 8 (0.5 g), Compound 10 (0.5 g), Aluminum Oxide C (produced by Nippon Aerosil; crystal grain size: 0.013 μm; average secondary particle size (observed through SEM): about 0.1 μm; BET specific surface area: 100 m$^2$/g) (0.33 g) subjected to heat treatment at 1,000° C., EC (1.8 g), EMC (4.2 g), LiPF$_6$ (battery grade produced by Hashimoto Kasei) (0.60 g) and Lucirin TPO (produced by BASF) (0.005 g) were thoroughly mixed in an argon atmosphere to obtain a photopolymerizable composition. This composition had a moisture content (by Karl Fischer's method) of 35 ppm.

The photopolymerizable composition obtained was applied on a PET film in an argon atmosphere and then irradiated with a chemical fluorescent lamp (FL20S.BL manufactured by Sankyo Denki) for 10 minutes. As a result, a copolymer (Compound 8 +Compound 10)/Aluminum Oxide C composite film impregnated with an EC/EMC-base electrolytic solution was obtained as a self-standing film having a thickness of about 30 μm. The resulting film had an ion conductivity at 25° C. or −20° C. measured by the impedance method, of 6.0×10$^{-3}$ S/cm or 1.5×10$^{-3}$ S/cm, respectively.

EXAMPLE 13
Production of Solid Polymer Electrolyte Film (Compound 8+Compound 10)

A thermopolymerizable composition was obtained in the same manner as in Example 12 except for adding PEROCTA ND (produced by Nippon Oils and Fats) (0.01 g) in place of Lucirin TPO (0.005 g) as an initiator and not using Aluminum Oxide C. This composition had a moisture content (by Karl Fischer's method) of 35 ppm.

The thermopolymerizable composition obtained was applied on a PET film in an argon atmosphere, covered with a PP film and heated on a hot plate at 60° C. for one hour. As a result, a copolymer (Compound 8+Compound 10) film impregnated with an EC/EMC-base electrolytic solution was obtained as a self-standing film having a thickness of about 30 μm. The resulting film had an ion conductivity at 25° C. or −20° C. measured by the impedance method, of 5.0×10$^{-3}$ S/cm or 1.2×10$^{-3}$ S/cm, respectively.

EXAMPLE 14
Production of Solid Polymer Electrolyte Composite Film (Compound 9)

A polymer (Compound 9)/Aluminum Oxide C composite film impregnated with an EC/EMC-base electrolytic solution was obtained as a self-standing film having a thickness of about 30 μm in the same manner as in Example 12 except for using Compound 9 (1.0 g) in place of Compounds 8 and 10. The resulting film had an ion conductivity at 25° C. or −20° C. measured by the impedance method, of 5.5×10$^{-3}$ S/cm or 1.2×10$^{-3}$ S/cm, respectively.

EXAMPLE 15
Production of Solid Polymer Electrolyte Composite Film (Compound 8+Compound 10):

A photopolymerizable composition was obtained in the same manner as in Example 12 except for using battery grade LIBF$_4$ (0.50 g) produced by Hashimoto Kasei in place of LiPF$_6$. This composition had a moisture content (by Karl Fischer's method) of 50 ppm.

The photopolymerizable composition obtained was applied on a PET film and irradiated with light in the same manner as in Example 12. As a result, a copolymer (Compound 8+Compound 10)/Aluminum Oxide C composite film impregnated with an EC/EMC-base electrolytic solution was obtained as a self-standing film having a thickness of about 30 μm. The resulting film had an ion conductivity at 25° C. or −20° C. measured by the impedance method, of 4.3×10$^{-3}$ S/cm or 0.8×10$^{-3}$ S/cm, respectively.

EXAMPLE 16
Production of Solid Polymer Electrolyte Composite Film (Compound 8+Compound 10)

A photopolymerizable composition was obtained in the same manner as in Example 12 except for using EC (1.5 g), EMC (3.0 g) and diethyl carbonate (DEC) (1.5 g) in place of EC/EMC. This composition had a moisture content (by Karl Fischer's method) of 35 ppm.

The photopolymerizable composition obtained was applied on a PET film in an argon atmosphere and then irradiated with a chemical fluorescent lamp for 10 minutes. As a result, a copolymer (Compound 8+Compound 10)/ Aluminum Oxide C composite film impregnated with an EC/EMC/DEC-base electrolytic solution was obtained as a self-standing film having a thickness of about 30 μm. The resulting film had an ion conductivity at 25° C. or −20° C. measured by the impedance method, of 5.0×10$^{-3}$ S/cm or 0.7×10$^{-3}$ S/cm, respectively.

EXAMPLE 17
Production of Solid Polymer Electrolyte Composite Film (Compound 8+Compound 10)

A photopolymerizable composition was obtained in the same manner as in Example 12 except for using hydrotalcite (KW2200, produced by Kyowa Kagaku, average particle size (observed through SEM): about 0.1 μm, BET specific surface area: 100 m$^2$/g) (0.33 g) subjected to heat treatment at 500° C. in place of Aluminum Oxide C. This composition had a moisture content (by Karl Fischer's method) of 50 ppm.

The photopolymerizable composition obtained was applied on a PET film in an argon atmosphere and then irradiated with a chemical fluorescent lamp for 10 minutes. As a result, a copolymer (Compound 8+Compound 10)/ KW2200 composite film impregnated with an EC/EMC-base electrolytic solution was obtained as a self-standing film having a thickness of about 30 μm. The resulting film had an ion conductivity at 25° C. or −20° C. measured by the impedance method, of 5.5×10$^{-3}$ S/cm or 1.2×10$^{-3}$ S/cm, respectively.

EXAMPLE 18
Production of Solid Polymer Electrolyte Composite Film (Compound 8+Compound 10)

A photopolymerizable composition was obtained in the same manner as in Example 12 except for using high-purity tetraethylammonium tetrafluoroborate (TEAB) (1.00 g) produced by Hashimoto Kasei in place of LiPF$_6$ and using propylene carbonate (6.0 g) in place of EC/EMC as a solvent. This composition had a moisture content (by Karl Fischer's method) of 100 ppm.

The photopolymerizable composition obtained was applied and irradiated with light in the same manner as in Example 12. As a result, a copolymer (Compound 8+Compound 10)/Aluminum Oxide C composite film impregnated with a PC-base electrolytic solution was obtained as a self-standing film having a thickness of about 30 μm. The resulting film had an ion conductivity at 25° C. or −20° C. measured by the impedance method, of 9.5×10$^{-3}$ S/cm or 1.6×10$^{-3}$ S/cm, respectively.

EXAMPLE 19
Production of Solid Polymer Electrolyte Film (Compound 8+Compound 10)

A thermopolymerizable composition was obtained in the same manner as in Example 18 except for adding benzoyl peroxide (0.02 g) in place of Lucirin TPO (0.005 g) as an initiator and not using Aluminum Oxide C. This composition had a moisture content (by Karl Fischer's method) of 120 ppm.

The thermopolymerizable composition obtained was coated on a PET film in an argon atmosphere, covered with a PP film and heated on a hot plate at 80° C. for one hour. As a result, a copolymer (Compound 8+Compound 10) film impregnated with a PC-base electrolytic solution was obtained as a self-standing film having a thickness of about 30 μm. The resulting film had an ion conductivity at 25° C. or −20° C. measured by the impedance method, of 9.0×10$^{-3}$ S/cm or 1.5×10$^{-3}$ S/cm, respectively.

EXAMPLE 20
Production of Solid Polymer Electrolyte Composite Film (Compound 8+Compound 10)

A salt-free photopolymerizable composition was obtained in the same manner as in Example 12 except for not using LiPF$_6$. This composition had a moisture content (by Karl Fischer's method) of 10 ppm.

The photopolymerizable composition obtained was applied and irradiated with light in the same manner as in Example 12. As a result, a salt-free copolymer (Compound 8+Compound 10)/Aluminum Oxide C composite film impregnated with an EC+EMC-base solvent was obtained as a self-standing film having a thickness of about 30 μm. The resulting film was dipped in 1.2 M LiPF$_6$/EC+EMC (3:7 by weight) electrolytic solution for about one hour so as to post-add the LiPF$_6$ salt into the film. This salt-post-added solid polymer electrolyte film had an ion conductivity at 25° C. or −20° C. measured by the impedance method, of 6.3×10$^{-3}$ S/cm or 2.0×10$^{-3}$ S/cm, respectively.

EXAMPLE 21
Production of Lithium Cobaltate Positive Electrode 11 g of $Li_2CO_3$ and 24 g of $Co_3O_4$ were thoroughly mixed, and the mixture was heated at 800° C. for 24 hours in an oxygen atmosphere and pulverized to obtain $LiCoO_2$ powder. The $LiCoO_2$ powder obtained, acetylene black and polyvinylidene fluoride were mixed at a weight ratio of 8:1:1 and thereto, an excess N-methylpyrrolidone solution was added to obtain a gel composition. This composition was applied on an aluminum foil of about 25 $\mu$m to have a size of 10 mm×10 mm and a thickness of about 180 $\mu$m. The coating was vacuum dried under heating at about 100° C. for 24 hours to obtain a lithium cobaltate positive electrode (75 mg).

EXAMPLE 22
Production of Graphite Negative Electrode

To a 8.6:0.4:1.0 (by weight) mixture of MCMB graphite (produced by Osaka Gas), graphite fiber grown by vapor phase method (produced by Showa Denko KK, average fiber diameter: 0.3 $\mu$m, average fiber length: 2.0 $\mu$m, heat-treated product at 2,700° C.) and polyvinylidene fluoride, an excess N-methylpyrrolidone solution was added to obtain a gel composition. This composition was applied on a copper foil of about 15 $\mu$m to have a size of 10 mm×10 mm and a thickness of about 250 $\mu$m. The coating was vacuum dried under heating at about 100° C. for 24 hours to obtain a graphite negative electrode (35 mg).

EXAMPLE 23
Production of Li Ion Secondary Battery

In a glove box of argon atmosphere, the salt-free copolymer (Compound 8+Compound 10)/Aluminum Oxide C composite film (12 mm×12 mm) prepared in Example 20 was laminated on the graphite negative electrode (10 mm×10 mm) prepared in Example 22 which was impregnated with an electrolytic solution (1.2M $LiPF_6$/EC+EMC (3:7)), and further thereon, the lithium cobaltate positive electrode (10 mm×10 mm) prepared in Example 21 and impregnated with an electrolytic solution (1.2M $LiPF_6$/EC+EMC (3:7)) was laminated. The edge portion of the battery was sealed with epoxy resin to obtain a graphite/cobalt oxide-base Li ion secondary battery having a construction shown in FIG. 1. This battery was charged and discharged at 60° C. or 25° C., a working voltage of from 2.75 to 4.1 V and an electric current of 0.5 mA, as a result, the maximum discharge capacity was 7.2 mAh or 7.2 mAh, respectively.

Further, the battery was repeatedly charged and discharged at 25° C., a working voltage of from 2.75 to 4.1V, a charge current of 0.5 mA and a discharge current of 3.0 mA, then the maximum discharge capacity was 7.0 mAh and the cycle life until the capacity was reduced to 50% was 480 times.

EXAMPLE 24
Production of Li Ion Secondary Battery

A Li ion secondary battery having a construction shown in FIG. 1 was produced in the same manner as in Example 23 except for using the solid polymer electrolyte (Compound 8+Compound 10)/KW2200 composite film prepared in Example 17 in place of the salt-free copolymer (Compound 8+Compound 10) /Aluminum Oxide C composite film.

The battery obtained was charged and discharged at 60° C. or 25° C., a working voltage of from 2.75 to 4.1 V and an electric current of 0.5 mA, as a result, the maximum discharge capacity was 7.2 mAh or 7.2 mAh, respectively.

Further, the battery was repeatedly charged and discharged at 25° C., a working voltage of from 2.75 to 4. 1V, a charge current of 0.5 mA and a discharge current of 3.0 mA, then the maximum discharge capacity was 6.6 mAh and the cycle life until the capacity was reduced to 50% was 510 times.

EXAMPLE 25
Production of Li Ion Secondary Battery

In a glove box of argon atmosphere, the (Compound 8+Compound 10)/Aluminum Oxide C-base photopolymerizable composition prepared in Example 12 was applied on the graphite negative electrode (10 mm×10 mm) prepared in Example 22 which was impregnated with an electrolytic solution (1M $LiPF_6$/EC+EMC (3:7)), to have a thickness of 30 $\mu$m. The coating was irradiated with a chemical fluorescent lamp for 10 minutes in an argon atmosphere to form a solid polymer electrolyte (Compound 8+Compound 10)/ Aluminum Oxide C composite film impregnated with an electrolytic solution directly on the graphite negative electrode. Further thereon, the lithium cobaltate positive electrode (10 mm×10 mm) impregnated with an electrolytic solution (1M $LiPF_6$/EC+EMC (3:7)) was laminated, and the edge portion of the battery was sealed with epoxy resin to obtain a graphite/cobalt oxide-base Li ion secondary battery having a construction shown in FIG. 1. This battery was charged and discharged at 60° C. or 25° C., a working voltage of from 2.75 to 4.1 V and an electric current of 0.5 mA, as a result, the maximum discharge capacity was 7.2 mAh or 7.2 mAh, respectively.

Further, the battery was repeatedly charged and discharged at 25° C., a working voltage of from 2.75 to 4.1 V, a charge current of 0.5 mA and a discharge current of 3.0 mA, then the maximum discharge capacity was 6.8 mAh and the cycle life until the capacity was reduced to 50% was 430 times.

EXAMPLE 26
Production of Li Ion Secondary Battery

In a glove box of argon atmosphere, the solid polymer electrolyte (Compound 8+Compound 10)/KW2200 composite film (12 mm×12 mm) prepared in Example 17 was laminated on the graphite negative electrode (10 mm×10 mm) prepared in Example 22 which was impregnated with the thermopolymerizable composition prepared in Example 13, and further thereon, the lithium cobaltate positive electrode (10 mm×10 mm) prepared in Example 21 and impregnated with the thermopolymerizable composition prepared in Example 13 was laminated. The edge portion of the battery was sealed with epoxy resin. This was heated at 60° C. for one hour to cure the thermopolymerizable composition, thereby obtaining a graphite/cobalt oxide-base Li ion secondary battery having a construction shown in FIG. 1. This battery was charged and discharged at 60° C. or 25° C., a working voltage of from 2.75 to 4.1 V and an electric current of 0.5 mA, as a result, the maximum discharge capacity was 7.2 mAh or 7.0 mAh, respectively.

Further, the battery was repeatedly charged and discharged at 25° C., a working voltage of from 2.75 to 4.1 V, a charge current of 0.5 mA and a discharge current of 3.0 mA, then the maximum discharge capacity was 5.0 mAh and the cycle life until the capacity was reduced to 50% was 280 times.

EXAMPLE 27
Production of Activated Carbon Electrode

To a 9.0:1.0 (by weight) mixture of coconut husk activated carbon and polyvinylidene fluoride, an excess N-methyl-pyrrolidone solution was added to obtain a gel composition. This composition was coated on a stainless steel foil to have a size of 10 mm×10 mm and a thickness of about 150 μm. The coating was vacuum dried at about 100° C. for 10 hours to obtain an activated carbon electrode (14.0 mg).

EXAMPLE 28
Production of Electric Double Layer Capacitor

In a glove box of argon atmosphere, two electrodes were prepared by impregnating an electrolytic solution (1M TEAB/PC+EC (3:1)) into the activated carbon electrode (14 mg) of 10 mm×10 mm prepared in Example 27. Then, the copolymer (Compound 8+Compound 10)/Aluminum Oxide C composite film (12 mm×12 mm) prepared in Example 18 was laminated to one electrode, then another electrode was laminated thereon, and the edge portion of the capacitor was sealed with an epoxy resin to produce an electric double layer capacitor having a construction shown in FIG. 2.

This capacitor was charged and discharged at 60° C. or 25° C., a working voltage of from 0 to 2.5 V and an electric current of 0.3 mA, as a result, the maximum capacity was 470 mF or 470 mF, respectively. The maximum capacity at 25° C. and 2.5 mA was 420 mF and the capacity scarcely changed even after the charging and discharging were repeated 50 times.

EXAMPLE 29
Production of Electric Double Layer Capacitor

In a glove box of argon atmosphere, two electrodes were prepared by impregnating the thermopolymerizable composition prepared in Example 19 into the activated carbon electrode (14 mg) of 10 mm×10 mm prepared in Example 27. Then, the copolymer (Compound 8+Compound 10)/Aluminum Oxide C composite film (12 mm×12 mm) prepared in Example 18 was laminated to one electrode, then another electrode was laminated thereon, the edge portion of the capacitor was sealed with an epoxy resin, and the thermopolymerizable composition was polymerized under heating at 80° C. for one hour to produce an electric double layer capacitor having a construction shown in FIG. 2.

This capacitor was charged and discharged at 60° C. or 25° C., a working voltage of from 0 to 2.5 V and an electric current of 0.3 mA, as a result, the maximum capacity was 460 mF or 430 mF, respectively. The maximum capacity at 25° C. and 2.5 mA was 250 mF and the capacity scarcely changed even after the charging and discharging were repeated 50 times.

EXAMPLE 30
Synthesis of Compounds 12 and 13

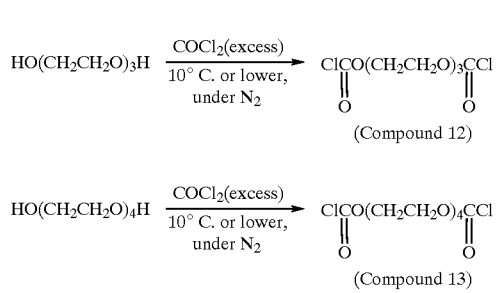

According to the formula (a') or (b'), excess phosgene gas was blown into triethylene glycol and tetraethylene glycol, at 10° C. or lower under nitrogen in an ordinary manner and reacted for about 5 hours to synthesize Compound 12 or Compound 13 as a bischloroformate form of respective triethylene glycol and tetraethylene glycol. The compounds were identified by GC-MS.

EXAMPLE 31
Oligomerization of Compounds 12 and 13 (Synthesis of Compounds 14 and 15)

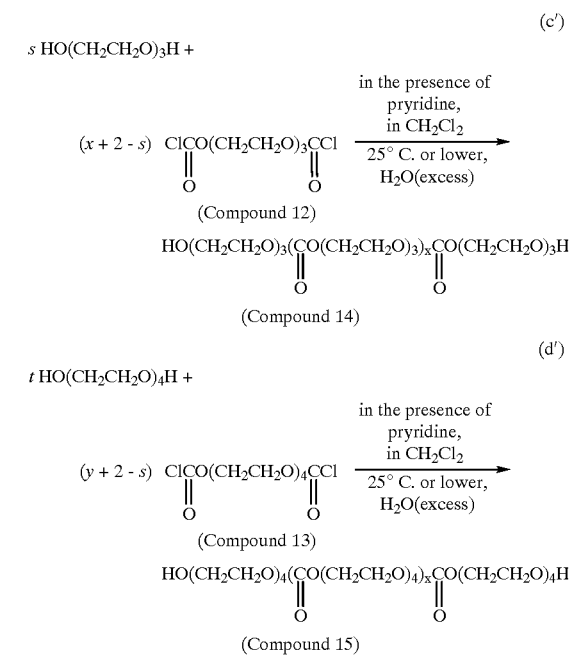

According to the formula (c') or (d'), the bischloroformate forms of triethylene glycol and tetraethylene glycol synthesized in Example 30 (Compound 12 or 13) and triethylene glycol and tetraethylene glycol, were reacted at 25° C. or lower for about 6 hours in the presence of pyridine in dichloromethane in an ordinary manner. Thereafter, excess water was added to hydroxylate the residual chloroformate terminal, thereby synthesizing oligoether/carbonates having a hydroxyl group at both terminals (Compound 14 or Compound 15).

The weight average molecular weight (Mw) and the average of repeating number x or y of each oligoether/carbonate, determined by the GPC analysis, are shown below.

Compound 14 Mw: up to about 1,200 X: up to about 5
Compound 15 Mw: up to about 1,500 Y: up to about 5

EXAMPLE 32
Synthesis of Compound 16

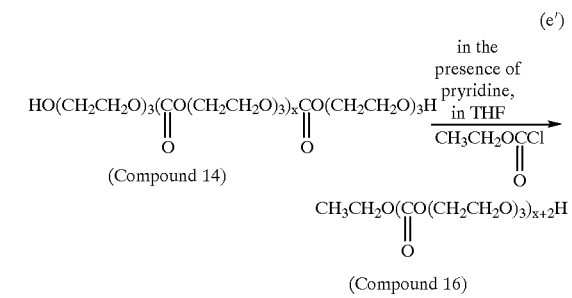

To an anhydrous THF solution of the ether/carbonate oligomer (Compound 14) synthesized in Example 31 according to formula (e'), an equimolar amount of ethyl chloroformate was gradually added dropwise at 25° C. or lower in the presence of pyridine by a usual method, and the resulting mixed solution was reacted for about 6 hours to synthesize an oligo ether/carbonate with one terminal being hydroxylated (Compound 16).

EXAMPLE 33
Synthesis of Polymerizable Compound 17

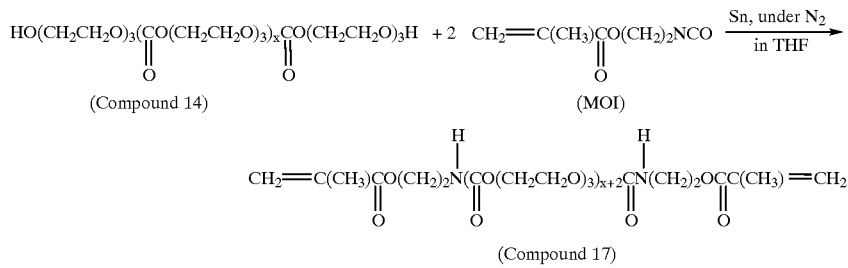
(Compound 14)    (MOI)

(Compound 17)

Compound 14 (average molecular weight: 1200) (60.0 g) and MOI (methacryloyloxyethyl isocyanate) (15.5 g) were dissolved in 200 ml of thoroughly purified THF in a nitrogen atmosphere, and thereto 0.44 g of dibutyltin dilaurate was added. Thereafter, the resulting mixed solution was reacted at 25° C. for about 15 hours, as a result, a colorless product was obtained. From the results of $^1$H-NMR, IR and elemental analysis thereof, it was found that Compound 14 and MOI were reacted at 1:2, the isocyanate group of MOI disappeared, a urethane bond was generated and Compound 17 was produced.

EXAMPLE 34
Synthesis of Polymerizable Compound 18

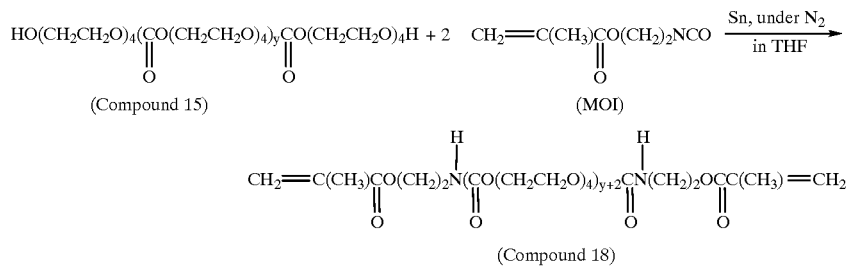
(Compound 15)    (MOI)

(Compound 18)

Compound 15 (average molecular weight: 1,500) (75.0 g) and MOI (15.5 g) were dissolved in thoroughly purified THF (200 ml) in a nitrogen atmosphere, and thereto dibutyltin dilaurate (0.44 g) was added. Thereafter, the resulting mixed solution was reacted at 25° C. for about 15 hours, as a result, a colorless product was obtained. From the results of $^1$H-NMR, IR and elemental analysis thereof, it was found that Compound 15 and MOI were reacted at 1:2, the isocyanate group of MOI disappeared, a urethane bond was generated and Compound 18 was produced.

EXAMPLE 35
Synthesis of Polymerizable Compound 19

$$CH_3CH_2(OC(OCH_2CH_2)_3)_{x+2}OH + CH_2\!=\!\!C(CH_3)CO(CH_2)_2NCO \xrightarrow[\text{in THF}]{\text{Sn, under } N_2}$$
(Compound 16)    (MOI)

$$CH_2\!=\!\!C(CH_3)CO(CH_2)_2NCO((CH_2CH_2O)_3CO)_{x+1}(CH_2CH_2O)_3COCH_2CH_3$$
(Compound 19)

Compound 16 (average molecular weight: 1,300) (130.0 g) and MOI (15.5 g) were dissolved in thoroughly purified THF (200 ml) in a nitrogen atmosphere, and thereto dibutyltin dilaurate (0.44 g) was added. Thereafter, the resulting mixed solution was reacted at 25° C. for about 15 hours, as a result, a colorless product was obtained. From the results of $^1$H-NMR, IR and elemental analysis thereof, it was found that Compound 16 and MOI were reacted at 1:1, the isocyanate group of MOI disappeared, a urethane bond was generated and Compound 19 was produced.

EXAMPLE 36
Production of Solid Polymer Electrolyte Film (Compound 17)

Compound 17 (2.0 g), ethylene carbonate (EC) (1.8 g), ethyl methyl carbonate (EMC) (4.2 g), LiPF$_6$ (battery grade produced by Hashimoto Kasei) (0.60 g) and 2,4,6-trimethylbenzoyldiphenyl phosphine oxide ("Lucirin TPO", trade name, produced by BASF) (0.010 g) were thoroughly mixed in an argon atmosphere to obtain a photopolymerizable composition. This composition had a moisture content (by Karl Fischer's method) of 30 ppm. The photopolymerizable composition obtained was applied on a PET film in an argon atmosphere and then irradiated with a chemical fluorescent lamp (FL20S.BL manufactured by Sankyo Denki) for 10 minutes. As a result, a polymer (Compound 17) film impregnated with an EC/EMC-base electrolytic solution was obtained as a self-standing film having a thickness of about 30 µm. The resulting film had an ion conductivity at 25° C. or –20° C. measured by the impedance method, of $4.0 \times 10^{-3}$ S/cm or $0.8 \times 10^{-3}$ S/cm, respectively.

EXAMPLE 37
Production of Solid Polymer Electrolyte Film (Compound 18)

A polymer (Compound 18) film impregnated with an EC/EMC-base electrolytic solution was obtained as a self-standing film having a thickness of about 30 µm in the same manner as in Example 36 except for using Compound 18 (2.0 g) in place of Compound 17. The resulting film had an ion conductivity at 25° C. or –20° C. measured by the impedance method, of $4.2 \times 10^{-3}$ S/cm or $0.8 \times 10^{-3}$ S/cm, respectively.

EXAMPLE 38
Production of Solid Polymer Electrolyte Film (Compound 18+Compound 19):

A copolymer (Compound 18+Compound 19) film impregnated with an EC/EMC-base electrolytic solution was obtained as a self-standing film having a thickness of about 30 µm in the same manner as in Example 36 except for using a mixture of Compound 18 (1.0 g) and Compound 19 (1.0 g) in place of Compound 17. The resulting film had an ion conductivity at 25° C. or –20° C. measured by the impedance method, of $4.5 \times 10^{-3}$ S/cm or $0.9 \times 10^{-3}$ S/cm, respectively.

EXAMPLE 39
Production of Solid Polymer Electrolyte Composite Film (Compound 17+Compound 18):

Compound 17 (0.5 g), Compound 18 (0.5 g), Aluminum Oxide C (produced by Nippon Aerosil; crystal grain size: 0.013 µm; average secondary particle size (observed through SEM): about 0. 1 µm; BET specific surface area: 100 m$^2$/g) (0.33 g) subjected to heat treatment at 1,000° C., EC (1.8 g), EMC (4.2 g), LiPF$_6$ (battery grade produced by Hashimoto Kasei) (0.60 g) and Lucirin TPO (produced by BASF) (0.005 g) were thoroughly mixed in an argon atmosphere to obtain a photopolymerizable composition. This composition had a moisture content (by Karl Fischer's method) of 35 ppm.

The photopolymerizable composition obtained was applied on a PET film in an argon atmosphere and then irradiated with a chemical fluorescent lamp (FL20S.BL manufactured by Sankyo Denki) for 10 minutes. As a result, a copolymer (Compound 17+Compound 18)/Aluminum Oxide C composite film impregnated with an EC/EMC-base electrolytic solution was obtained as a self-standing film having a thickness of about 30 µm. The resulting film had an ion conductivity at 25° C. or –20° C. measured by the impedance method, of $6.6 \times 10^{-3}$ S/cm or $1.8 \times 10^{-3}$ S/cm, respectively.

EXAMPLE 40
Production of Solid Polymer Electrolyte Film (Compound 17+Compound 18)

A thermopolymerizable composition was obtained in the same manner as in Example 39 except for adding PEROCTA ND (produced by Nippon Oils and Fats) (0.01 g) in place of Lucirin TPO (0.005 g) as an initiator and not using Aluminum Oxide C. This composition had a moisture content (by Karl Fischer's method) of 40 ppm.

The thermopolymerizable composition obtained was applied on a PET film in an argon atmosphere, covered with a PP film and heated on a hot plate at 60° C. for one hour. As a result, a copolymer (Compound 17+Compound 18) film impregnated with an EC/EMC-base electrolytic solution was obtained as a self-standing film having a thickness of about 30 µm. The resulting film had an ion conductivity at 25° C. or –20° C. measured by the impedance method, of $6.0 \times 10^{-3}$ S/cm or $1.5 \times 10^{-3}$ S/cm, respectively.

EXAMPLE 41
Production of Solid Polymer Electrolyte Composite Film (Compound 17+Compound 18)

A photopolymerizable composition was obtained in the same manner as in Example 39 except for using battery grade LiBF$_4$ (0.50 g) produced by Hashimoto Kasei in place of LiPF$_6$. This composition had a moisture content (by Karl Fischer's method) of 50 ppm.

The photopolymerizable composition obtained was applied on a PET film and irradiated with light in the same manner as in Example 39. As a result, a copolymer (Compound 17+Compound 18)/Aluminum Oxide C composite film impregnated with an EC/EMC-base electrolytic solution was obtained as a self-standing film having a thickness of about 30 µm. The resulting film had an ion conductivity at 25° C. or –20° C. measured by the impedance method, of $5.0 \times 10^{-3}$ S/cm or $0.9 \times 10^3$ S/cm, respectively.

EXAMPLE 42
Production of Solid Polymer Electrolyte Composite Film (Compound 17+Compound 18)

A photopolymerizable composition was obtained in the same manner as in Example 39 except for using EC (1.5 g), EMC (3.0 g) and diethyl carbonate (DEC) (1.5 g) in place of EC/EMC. This composition had a moisture content (by Karl Fischer's method) of 35 ppm.

The photopolymerizable composition obtained was applied on a PET film in an argon atmosphere and then irradiated with a chemical fluorescent lamp for 10 minutes. As a result, a copolymer (Compound 17+Compound 18)/Aluminum Oxide C composite film impregnated with an EC/EMC/DEC-base electrolytic solution was obtained as a self-standing film having a thickness of about 30 µm. The resulting film had an ion conductivity at 25° C. or –20° C. measured by the impedance method, of $5.8 \times 10^{-3}$ S/cm or $1.0 \times 10^{-3}$ S/cm, respectively.

EXAMPLE 43
Production of Solid Polymer Electrolyte Composite Film (Compound 17+Compound 18)

A photopolymerizable composition was obtained in the same manner as in Example 39 except for using hydrotalcite (KW2200, produced by Kyowa Kagaku, average particle size (observed through SEM): about 0.1 μm, BET specific surface area: 100 m²/g) (0.33 g) subjected to heat treatment at 500° C. in place of Aluminum Oxide C. This composition had a moisture content (by Karl Fischer's method) of 45 ppm.

The photopolymerizable composition obtained was applied on a PET film in an argon atmosphere and then irradiated with a chemical fluorescent lamp for 10 minutes. As a result, a copolymer (Compound 17+Compound 18)/KW2200 composite film impregnated with an EC/EMC-base electrolytic solution was obtained as a self-standing film having a thickness of about 30 μm. The resulting film had an ion conductivity at 25° C. or −20° C. measured by the impedance method, of $6.0 \times 10^{-3}$ S/cm or $1.4 \times 10^{-3}$ S/cm, respectively.

EXAMPLE 44
Production of Solid Polymer Electrolyte Film (Compound 17+Compound 18)

A photopolymerizable composition was obtained in the same manner as in Example 39 except for using high-purity tetraethylammonium tetrafluoroborate (TEAB) (1.00 g) produced by Hashimoto Kasei in place of $LiPF_6$ and using propylene carbonate (6.0 g) in place of EC/EMC as a solvent. This composition had a moisture content (by Karl Fischer's method) of 110 ppm.

The photopolymerizable composition obtained was applied and irradiated with light in the same manner as in Example 39. As a result, a copolymer (Compound 17+Compound 18)/Aluminum Oxide C composite film impregnated with a PC-base electrolytic solution was obtained as a self-standing film having a thickness of about 30 μm. The resulting film had an ion conductivity at 25° C. or −20° C. measured by the impedance method, of $10.5 \times 10^{-3}$ S/cm or $1.8 \times 10^{-3}$ S/cm, respectively.

EXAMPLE 45
Production of Solid Polymer Electrolyte Film (Compound 17+Compound 18)

A thermopolymerizable composition was obtained in the same manner as in Example 44 except for adding benzoyl peroxide (0.02 g) in place of Lucirin TPO (0.005 g) as an initiator and not using Aluminum Oxide C. This composition had a moisture content (by Karl Fischer's method) of 120 ppm.

The thermopolymerizable composition obtained was coated on a PET film in an argon atmosphere, covered with a PP film and heated on a hot plate at 80° C. for one hour. As a result, a copolymer (Compound 17+Compound 18) film impregnated with a PC-base electrolytic solution was obtained as a self-standing film having a thickness of about 30 μm. The resulting film had an ion conductivity at 25° C. or −20° C. measured by the impedance method, of $11.0 \times 10^{-3}$ S/cm or $2.0 \times 10^{-3}$ S/cm, respectively.

EXAMPLE 46
Production of Solid Polymer Electrolyte Composite Film (Compound 17+Compound 18)

A salt-free photopolymerizable composition was obtained in the same manner as in Example 39 except for not using $LiPF_6$. This composition had a moisture content (by Karl Fischer's method) of 10 ppm.

The photopolymerizable composition obtained was applied and irradiated with light in the same manner as in Example 39. As a result, a salt-free copolymer (Compound 17+Compound 18)/Aluminum Oxide C composite film impregnated with an EC+EMC-base solvent was obtained as a self-standing film having a thickness of about 30 μm. The resulting film was dipped in 1.2 M $LiPF_6$/EC+EMC (3:7 by weight) electrolytic solution for about one hour so as to post-add the $LiPF_6$ salt into the film. This salt-post-added solid polymer electrolyte film had an ion conductivity at 25° C. or −20° C. measured by the impedance method, of $7.0 \times 10^{-3}$ S/cm or $2.0 \times 10^{-3}$ S/cm, respectively.

EXAMPLE 47
Production of Li Ion Secondary Battery

In a glove box of argon atmosphere, the salt-free copolymer (Compound 17+Compound 18)/Aluminum Oxide C composite film (12 mm×12 mm) prepared in Example 46 was laminated on the graphite negative electrode (10 mm×10 mm) prepared in Example 22 which was impregnated with an electrolytic solution (1.2M $LiPF_6$/EC+EMC (3:7)), and further thereon, the lithium cobaltate positive electrode (10 mm×10 mm) prepared in Example 21 and impregnated with an electrolytic solution (1.2M $LiPF_6$/EC+EMC (3:7)) was laminated. The edge portion of the battery was sealed with epoxy resin to obtain a graphite/cobalt oxide-base Li ion secondary battery having a construction shown in FIG. 1.

This battery was charged and discharged at 60° C. or 25° C., a working voltage of from 2.75 to 4.1 V and an electric current of 0.5 mA, as a result, the maximum discharge capacity was 7.2 mAh or 7.2 mAh, respectively.

Further, the battery was repeatedly charged and discharged at 25° C., a working voltage of from 2.75 to 4.1 V, a charge current of 0.5 mA and a discharge current of 3.5 mA, then the maximum discharge capacity was 7.0 mAh and the cycle life until the capacity was reduced to 50% was 530 times.

EXAMPLE 48
Production of Li Ion Secondary Battery

A Li ion secondary battery having a construction shown in FIG. 1 was produced in the same manner as in Example 47 except for using the solid polymer electrolyte (Compound 17+Compound 18)/KW2200 composite film prepared in Example 43 in place of the salt-free copolymer (Compound 17+Compound 18) /Aluminum Oxide C composite film.

The battery obtained was charged and discharged at 60° C. or 25° C., a working voltage of from 2.75 to 4.1 V and an electric current of 0.5 mA, as a result, the maximum discharge capacity was 7.2 mAh or 7.2 mAh, respectively.

Further, the battery was repeatedly charged and discharged at 25° C., a working voltage of from 2.75 to 4.1 V, a charge current of 0.5 mA and a discharge current of 3.0 mA, then the maximum discharge capacity was 6.8 mAh and the cycle life until the capacity was reduced to 50% was 560 times.

EXAMPLE 49
Production of Li Ion Secondary Battery

In a glove box of argon atmosphere, the (Compound 17+Compound 18)/Aluminum Oxide C-base photopolymerizable composition prepared in Example 41 was applied on the graphite negative electrode (10 mm×10 mm) prepared in Example 22 which was impregnated with an electrolytic solution (1M $LiPF_6$/EC+EMC (3:7)), to have a thickness of 30 μm. The coating was irradiated with a chemical fluorescent lamp for 10 minutes in an argon atmosphere to form a solid polymer electrolyte (Compound 17+Compound 18)/ Aluminum Oxide C composite film impregnated with an electrolytic solution directly on the graphite negative electrode. Further thereon, the lithium cobaltate positive electrode (10 mm×10 mm) prepared in Example 21 impregnated with an electrolytic solution (IM $LiPF_6$/EC+EMC (3:7)) was laminated, and the edge portion of the battery was sealed with epoxy resin to obtain a graphite/cobalt oxide-base Li ion secondary battery having a construction shown in FIG. 1.

This battery was charged and discharged at 60° C. or 25° C., a working voltage of from 2.75 to 4.1 V and an electric current of 0.5 mA, as a result, the maximum discharge capacity was 7.2 mAh or 7.2 mAh, respectively.

Further, the battery was repeatedly charged and discharged at 25° C., a working voltage of from 2.75 to 4.1 V, a charge current of 0.5 mA and a discharge current of 3.5 mA, then the maximum discharge capacity was 6.8 mAh and the cycle life until the capacity was reduced to 50% was 475 times.

EXAMPLE 50
Production of Li Ion Secondary Battery

In a glove box of argon atmosphere, the solid polymer electrolyte (Compound 17+Compound 18)/KW2200 composite film (12 mm×12 mm) prepared in Example 43 was laminated on the graphite negative electrode (10 mm×10 mm) prepared in Example 22 which was impregnated with the thermopolymerizable composition (Compound 17+Compound 18) prepared in Example 40, and further thereon, the lithium cobaltate positive electrode (10 mm×10 mm) prepared in Example 21 and impregnated with the thermopolymerizable composition prepared in Example 40 was laminated. The edge portion of the battery was sealed with epoxy resin. This was heated at 60° C. for one hour to cure the thermopolymerizable composition, thereby obtaining a graphite/cobalt oxide-base Li ion secondary battery having a construction shown in FIG. 1.

This battery was charged and discharged at 60° C. or 25° C., a working voltage of from 2.75 to 4.1 V and an electric current of 0.5 mA, as a result, the maximum discharge capacity was 7.2 mAh or 7.2 mAh, respectively.

Further, the battery was repeatedly charged and discharged at 25° C., a working voltage of from 2.75 to 4.1 V, a charge current of 0.5 mA and a discharge current of 3.5 mA, then the maximum discharge capacity was 5.8 mAh and the cycle life until the capacity was reduced to 50% was 360 times.

EXAMPLE 51
Production of Electric Double Layer Capacitor

In a glove box of argon atmosphere, two electrodes were prepared by impregnating an electrolytic solution (1M TEAB/PC+EC (3:1)) into the activated carbon electrode (14 mg) of 10 mm×10 mm prepared in Example 27. Then, the copolymer (Compound 17+Compound 18)/Aluminum Oxide C composite film (12 mm×12 mm) prepared in Example 44 was laminated to one electrode, then another electrode was laminated thereon, and the edge portion of the capacitor was sealed with an epoxy resin to produce an electric double layer capacitor having a construction shown in FIG. 2.

This capacitor was charged and discharged at 60° C. or 25° C., a working voltage of from 0 to 2.5 V and an electric current of 0.3 mA, as a result, the maximum capacity was 470 mF or 470 mF, respectively. The maximum capacity at 25° C. and 2.5 mA was 445 mF and the capacity scarcely changed even after the charging and discharging were repeated 50 times.

EXAMPLE 52
Production of Electric Double Layer Capacitor

In a glove box of argon atmosphere, two electrodes were prepared by impregnating the thermopolymerizable composition prepared in Example 45 into the activated carbon electrode (14 mg) of 10 mm×10 mm prepared in Example 27. Then, the copolymer (Compound 17+Compound 18)/ Aluminum Oxide C composite film (12 mm×12 mm) prepared in Example 44 was laminated to one electrode, then another electrode was laminated thereon, the edge portion of the capacitor was sealed with an epoxy resin, and the thermopolymerizable composition was polymerized under heating at 80° C. for one hour to produce an electric double layer capacitor having a construction shown in FIG. 2.

This capacitor was charged and discharged at 60° C. or 25° C., a working voltage of from 0 to 2.5 V and an electric current of 0.3 mA, as a result, the maximum capacity was 460 mF or 450 mF, respectively. The maximum capacity at 25° C. and 2.5 mA was 300 mF and the capacity scarcely changed even after the charging and discharging were repeated 50 times.

INDUSTRIAL APPLICABILITY

The highly ion conductive solid polymer electrolyte comprising a polymer having a cross-linked and/or side chain group mainly comprising a poly- or oligo-carbonate group, and an electrolyte salt of the present invention has good film strength, high ion conductivity at a range from a low temperature to a high temperature and excellent workability and as compared with conventional solid polymer electrolytes having an oligooxyalkyelne-base cross-linked and/or side chain group, is superior in the large current characteristics and high-temperature durability.

The battery or electric double layer capacitor using the solid polymer electrolyte of the present invention has no fear of liquid leakage and can be stably used for a long period of time because the ion conductive material thereof is a solid. Further, by using the solid electrolyte, a thin battery or capacitor can be produced.

Furthermore, by using the solid polymer electrolyte of the present invention, a secondary battery facilitated in the formation into a thin film, capable of high-capacity working, having a long life and having excellent properties with respect to the large current characteristics, high-temperature durability, reliability, stability and workability, can be obtained. This secondary battery can work in high capacity and high current as the entirely solid-type battery and has good cycle property and is excellent in the safety and reliability, and this battery can be used as a power source for electric products including a main power source of portable instruments and a backup power source, or as a large-scale power source for electric automobiles or for load leveling. Since formation into a thin film is facilitated, the battery can also be used as a paper battery for indication cards and the like.

Further, by using the solid polymer electrolyte of the present invention, an electric double layer capacitor having high output voltage, large takeout current, long life and excellent properties with respect to high-temperature durability, workability, reliability and stability, can be obtained. The electric double layer capacitor of the present invention can work in high voltage, high capacity and high current as compared with conventional capacitors, has good cycle property and is excellent in the safety and reliability, accordingly, this can be used not only as a backup power source but by using it in combination with a small battery, also as a power source for various electric products. The capacitor also has excellent workability such as formation into a thin film and the like and therefore, use thereof can be expected to expand over the conventional use as an electric double layer capacitor.

What is claimed is:

1. A solid polymer electrolyte comprising at least one polymer compound having a poly- or oligo-carbonate group represented by formula (1):

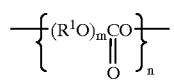
(1)

wherein $R^1$ represents a chained, branched and/or cyclic divalent group having from 1 to 10 carbon atoms, which may contain a hetero atom, m represents an integer of from 3 to 10 and n represents an integer of from 2 to 1,000, provided that $R^1$, m and n which are present in plurality in the same molecule may be the same or different, respectively, and at least one electrolyte salt.

2. The solid polymer electrolyte as claimed in claim 1, wherein the polymer compound contains a poly- or oligo-carbonate group represented by the general formula (1) and is obtained by utilizing a polymerization reaction using a polymerizable functional group represented by the following formula (2) and/or formula (3):

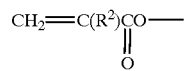
(2)

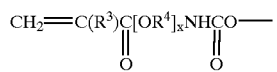
(3)

wherein $R^2$ and $R^3$ each represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^2$, $R^3$, $R^4$ and x which are present in plurality in the same molecule may be the same or different, respectively.

3. The solid polymer electrolyte as claimed in claim 1 or 2, which contains at least one organic solvent.

4. The solid polymer electrolyte as claimed in claim 3, wherein the organic solvent is a carbonate-base compound.

5. The solid polymer electrolyte as claimed in claim 1 or 2, which contains at least one inorganic oxide.

6. The solid polymer electrolyte as claimed in claim 1 or 2, wherein the electrolyte salt is selected from an alkali metal salt, a quaternary ammonium salt and a quaternary phosphonium salt.

7. A solid polymer electrolyte comprising:

(i) at least one polymer compound which contains a poly- or oligo-carbonate group represented by formula (1):

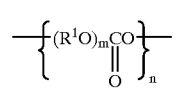
(1)

wherein $R^1$ represents a chained, branched and/or cyclic divalent group having from 1 to 10 carbon atoms, which may contain a hetero atom, m represents an integer of from 3 to 10 and n represents an integer of from 2 to 1,000, provided that $R^1$, m and n which are present in plurality in the same molecule may be the same or different, respectively, and is obtained by utilizing a polymerization reaction using a polymerizable functional group represented by the following formula (2) and/or formula (3):

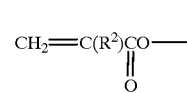
(2)

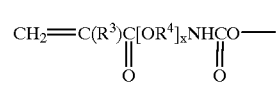
(3)

wherein $R^2$ and $R^3$ each represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^2$, $R^3$, $R^4$ and x which are present in plurality in the same molecule may be the same or different, respectively;

(ii) at least one organic solvent;

(iii) at least one inorganic oxide; and (iv) at least one electrolyte salt.

8. The solid polymer electrolyte as claimed in claim 7, wherein the organic solvent is a carbonate-base compound.

9. The solid polymer electrolyte as claimed in claim 7 or 8, wherein the electrolyte salt is selected from an alkali metal salt, a quaternary ammonium salt and a quaternary phosphonium salt.

10. A solid polymer electrolyte comprising at least one polymer compound which contains a poly- or oligo-carbonate group represented by formula (1'):

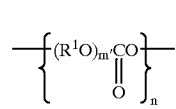
(1')

wherein $R^1$ represents a chained, branched and/or cyclic divalent group having from 1 to 10 carbon atoms, which may contain a hetero atom, n represents an integer of from 2 to 1,000, m' represents 1 or 2, provided that $R^1$, m' and n which are present in plurality in the same molecule may be the same or different, respectively, and is obtained by utilizing a polymerization reaction using a polymerizable functional group represented by the following formula (3):

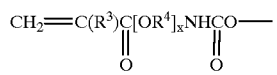

(3)

wherein $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^3$, $R^4$ and x which are present in plurality in the same molecule may be the same or different, respectively, and at least one electrolyte salt.

11. The solid polymer electrolyte as claimed in claim 10, which contains at least one organic solvent.

12. The solid polymer electrolyte as claimed in claim 11, wherein the organic solvent is a carbonate-base compound.

13. The solid polymer electrolyte as claimed in claim 10, which contains at least one inorganic oxide.

14. The solid polymer electrolyte as claimed in claim 10, wherein the electrolyte salt is selected from an alkali metal salt, a quaternary ammonium salt and a quaternary phosphonium salt.

15. A solid polymer electrolyte comprising:
(i) at least one polymer compound which contains a poly- or oligo-carbonate group represented by formula (1'):

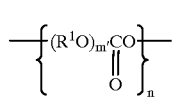

(1')

wherein $R^1$ represents a chained, branched and/or cyclic divalent group having from 1 to 10 carbon atoms, which may contain a hetero atom, n represents an integer of from 2 to 1,000, m' represents 1 or 2, provided that $R^1$, m' and n which are present in plurality in the same molecule may be the same or different, respectively, and is obtained by utilizing a polymerization reaction using a polymerizable functional group represented by the following formula (3):

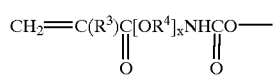

(3)

wherein $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^3$, $R^4$ and x which are present in plurality in the same molecule may be the same or different, respectively;

(ii) at least one organic solvent;
(iii) at least one inorganic oxide; and
(iv) at least one electrolyte salt.

16. The solid polymer electrolyte as claimed in claim 15, wherein the organic solvent is a carbonate-base compound.

17. The solid polymer electrolyte as claimed in claim 15 or 16, wherein the electrolyte salt is selected from an alkali metal salt, a quaternary ammonium salt and a quaternary phosphonium salt.

18. A battery using the solid polymer electrolyte described in of claim 1.

19. The lithium battery as claimed in claim 18, wherein the negative electrode used in the battery is at least one material selected from lithium, lithium alloy, a carbon material capable of occluding and releasing lithium ion, an inorganic oxide capable of occluding and releasing lithium ion, an inorganic chalcogenide capable of occluding and releasing lithium ion, and an electroconductive polymer compound capable of occluding and releasing lithium ion.

20. An electric double layer capacitor comprising polarizable electrodes disposed through an ion conductive material, wherein the ion conductive material is a solid polymer electrolyte described in of claim 1.

21. A polymerizable compound represented by formula (4):

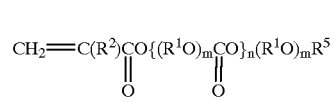

(4)

wherein $R^1$ represents a chained, branched and/or cyclic divalent group having from 1 to 10 carbon atoms, which may contain a hetero atom, $R^2$ represents a hydrogen atom or an alkyl group having from 1 to 6 carbon atoms, $R^5$ represents a chained, branched and/or cyclic organic group having from 1 to 20 carbon atoms, which may contain a hetero atom, m represents an integer of from 3 to 10, and n represents an integer of from 2 to 1,000, provided that $R^1$, $R^2$, m and n which are present in plurality in the same molecule may be the same or different, respectively.

22. A polymerizable compound represented by formula (5):

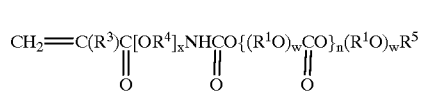

(5)

wherein $R^1$ and $R^4$ each represents a chained, branched and/or cyclic divalent group having from 1 to 10 carbon atoms, which may contain a hetero atom, $R^3$ represents a hydrogen atom or an alkyl group having from 1 to 6 carbon atoms, $R^5$ represents a chained, branched and/or cyclic organic group having from 1 to 20 carbon atoms, which may contain a hetero atom, w represents an integer of from 1 to 10 carbon atoms, n represents an integer of from 2 to 1,000, and x represents 0 or an integer of from 1 to 10, provided that $R^1$, $R^3$, $R^4$, w, n and x which are present in plurality in the same molecule may be the same or different, respectively.

23. A process for producing a solid polymer electrolyte, comprising disposing at least one heat and/or active ray polymerizable compound having a poly- or oligo-carbonate group represented by formula (1):

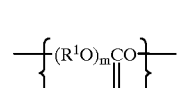

(1)

wherein $R^1$ represents a chained, branched and/or cyclic divalent group having from 1 to 10 carbon atoms, which may contain a hetero atom, m represents an integer of from 3 to 10 and n represents an integer from 2 to 1,000, provided that $R^1$, m and n which are present in plurality in the same molecule may be the same or different, respectively, and a polymerizable functional group represented by formula (2)

and/or formula (3):

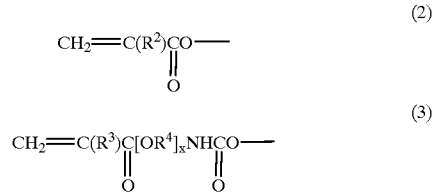

wherein $R^2$ and $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^2$, $R^3$, $R^4$ and x which are present in plurality in the same molecule may be the same or different, respectively, and a polymerizable composition containing at least one electrolyte salt or further containing at least one organic solvent and/or at least one inorganic oxide on a support, and polymerizing the polymerizable composition.

24. A process for producing a solid polymer electrolyte, comprising disposing at least one heat and/or active ray polymerizable compound having a poly- or oligo-carbonate group represented by formula (1):

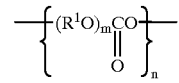

wherein $R^1$ represents a chained, branched and/or cyclic divalent group having from 1 to 10 carbon atoms, which may contain a hetero atom, m represents an integer of from 3 to 10 and n represents an integer from 2 to 1,000, provided that $R^1$, m and n which are present in plurality in the same molecule may be the same or different, respectively, and a polymerizable functional group represented by formula (2) and/or formula (3):

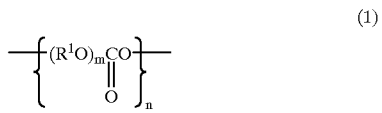

wherein $R^2$ and $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^2$, $R^3$, $R^4$ and x which are present in plurality in the same molecule may be the same or different, respectively, and a polymerizable composition containing at least one organic solvent or further containing at least one inorganic oxide on a support, polymerizing the polymerizable composition, and contacting the polymer obtained with an electrolytic solution to impregnate an electrolyte salt.

25. A process for producing a battery, comprising placing at least one heat and/or active ray polymerizable compound having a poly- or oligo-carbonate group represented by formula (1):

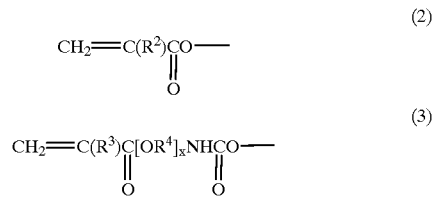

wherein $R^1$ represents a chained, branched and/or cyclic divalent group having from 1 to 10 carbon atoms, which may contain a hetero atom, m represents an integer of from 3 to 10 and n represents an integer from 2 to 1,000, provided that $R^1$, m and n which are present in plurality in the same molecule may be the same or different, respectively, and a polymerizable functional group represented by formula (2) and/or formula (3):

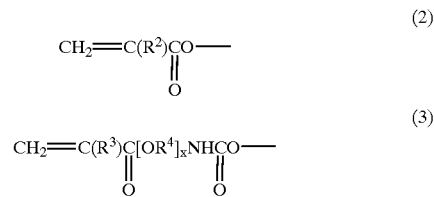

wherein $R^2$ and $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^2$, $R^3$, $R^4$ and x which are present in plurality in the same molecule may be the same or different, respectively, and a polymerizable composition containing at least one electrolyte salt or further containing at least one organic solvent and/or at least one inorganic oxide in a structure for constructing a battery or disposing these on a support, and polymerizing the polymerizable composition.

26. A process for producing a battery, comprising placing at least one heat and/or active ray polymerizable compound having a poly- or oligo-carbonate group represented by formula (1):

wherein $R^1$ represents a chained, branched and/or cyclic divalent group having from 1 to 10 carbon atoms, which may contain a hetero atom, m represents an integer of from 3 to 10 and n represents an integer from 2 to 1,000, provided that $R^1$, m and n which are present in plurality in the same molecule may be the same or different, respectively, and a polymerizable functional group represented by formula (2) and/or formula (3):

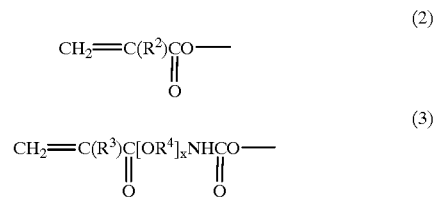

wherein $R^2$ and $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^2$, $R^3$, $R^4$ and x which are present in plurality in the same molecule may be the same or different, respectively, and a polymerizable composition containing at least organic solvent or further containing at least one inorganic oxide in a structure for constructing a battery or disposing these on a support, and contacting the polymer obtained with an electrolytic solution to impregnate an electrolyte salt.

27. A process for producing an electric double layer capacitor, comprising placing at least one heat and/or active ray polymerizable compound having a poly- or oligo-carbonate group represented by formula (1):

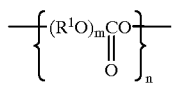

(1)

wherein $R^1$ represents a chained, branched and/or cyclic divalent group having from 1 to 10 carbon atoms, which may contain a hetero atom, m represents an integer of from 3 to 10 and n represents an integer from 2 to 1,000, provided that $R^1$, m and n which are present in plurality in the same molecule may be the same or different, respectively, and a polymerizable functional group represented by formula (2) and/or formula (3):

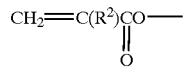

(2)

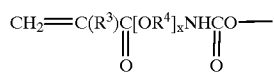

(3)

wherein $R^2$ and $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^2$, $R^3$, $R^4$ and x which are present in plurality in the same molecule may be the same or different, respectively, and a polymerizable composition containing at least one electrolyte salt or further containing at least one organic solvent and/or at least one inorganic oxide in a structure for constructing an electric double layer capacitor or disposing these on a support, and polymerizing the polymerizable composition.

28. A process for producing an electric double layer capacitor, comprising placing at least one heat and/or active ray polymerizable compound having a poly- or oligo-carbonate group represented by formula (1):

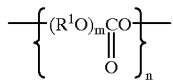

(1)

wherein $R^1$ represents a chained, branched and/or cyclic divalent group having from 1 to 10 carbon atoms, which may contain a hetero atom, m represents an integer of from 3 to 10 and n represents an integer from 2 to 1,000, provided that $R^1$, m and n which are present in plurality in the same molecule may be the same or different, respectively, and a polymerizable functional group represented by formula (2) and/or formula (3):

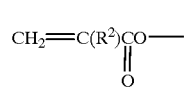

(2)

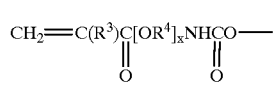

(3)

wherein $R^2$ and $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^2$, $R^3$, $R^4$ and x which are present in plurality in the same molecule may be the same or different, respectively, and a polymerizable composition containing at least one organic solvent or further containing at least one inorganic oxide in a structure for constructing an electric double layer capacitor or disposing these on a support, polymerizing the polymerizable composition, and contacting the polymer obtained with an electrolytic solution to impregnate an electrolyte salt.

29. A process for producing a solid polymer electrolyte, comprising disposing at least one heat and/or active ray polymerizable compound having a poly- or oligo-carbonate group represented by formula (1'):

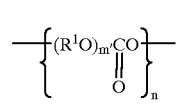

(1')

wherein $R^1$ represents a chained, branched and/or cyclic divalent group having from 1 to 10 carbon atoms, which may contain a hetero atom, n represents an integer of from 2 to 1,000, m' represents 1 or 2, provided that $R^1$, m' and n which are present in plurality in the same molecule may be the same or different, respectively, and a polymerizable functional group represented by the following formula (3):

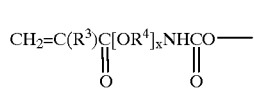

(3)

wherein $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^3$, $R^4$ and x which are present in plurality in the same molecule may be the same or different, respectively, and a polymerizable composition containing at least one electrolyte salt or further containing at least one organic solvent and/or at least one inorganic oxide on a support, and polymerizing the polymerizable composition.

30. A process for producing a solid polymer electrolyte, comprising disposing at least one heat and/or active ray polymerizable compound having a poly- or oligo-carbonate group represented by formula (1'):

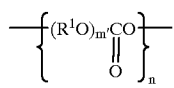

(1')

wherein $R^1$ represents a chained, branched and/or cyclic divalent group having from 1 to 10 carbon atoms, which may contain a hetero atom, n represents an integer of from 2 to 1,000, m' represents 1 or 2, provided that $R^1$, m' and n which are present in plurality in the same molecule may be the same or different, respectively, and a polymerizable functional group represented by the following formula (3):

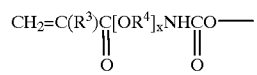

(3)

wherein $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^3$, $R^4$ and x which are present in plurality in the same molecule may be the same or different, respectively, and a polymerizable composition containing at least one organic solvent or further containing at least one inorganic oxide on a support, polymerizing the polymerizable composition, and contacting the polymer obtained with an electrolytic solution to impregnate an electrolyte salt.

31. A process for producing a battery, comprising placing at least one heat and/or active ray polymerizable compound having a poly- or oligo-carbonate group represented by formula (1'):

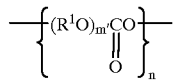

(1')

wherein $R^1$ represents a chained, branched and/or cyclic divalent group having from 1 to 10 carbon atoms, which may contain a hetero atom, n represents an integer of from 2 to 1,000, m' represents 1 or 2, provided that $R^1$, m' and n which are present in plurality in the same molecule may be the same or different, respectively, and a polymerizable functional group represented by the following formula (3):

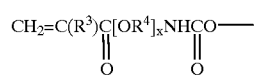

(3)

wherein $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^3$, $R^4$ and x which are present in plurality in the same molecule may be the same or different, respectively, and a polymerizable composition containing at least one electrolyte salt or further containing at least one organic solvent and/or at least one inorganic oxide in a structure for constructing a battery or disposing these on a support, and polymerizing the polymerizable composition.

32. A process for producing a battery, comprising placing at least one heat and/or active ray polymerizable compound having a poly- or oligo-carbonate group represented by formula (1'):

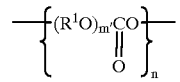

(1')

wherein $R^1$ represents a chained, branched and/or cyclic divalent group having from 1 to 10 carbon atoms, which may contain a hetero atom, n represents an integer of from 2 to 1,000, m' represents 1 or 2, provided that $R^1$, m' and n which are present in plurality in the same molecule may be the same or different, respectively, and a polymerizable functional group represented by the following formula (3):

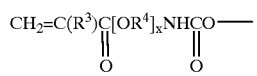

(3)

wherein $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^3$, $R^4$ and x which are present in plurality in the same molecule may be the same or different, respectively, and a polymerizable composition containing at least one organic solvent or further containing at least one inorganic oxide in a structure for constructing a battery or disposing these on a support, and contacting the polymer obtained with an electrolytic solution to impregnate an electrolyte salt.

33. A process for producing an electric double layer capacitor, comprising placing at least one heat and/or active ray polymerizable compound which contains a poly- or oligo-carbonate group represented by formula (1'):

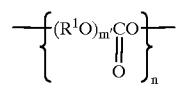

(1')

wherein $R^1$ represents a chained, branched and/or cyclic divalent group having from 1 to 10 carbon atoms, which may contain a hetero atom, n represents an integer of from 2 to 1,000, m' represents 1 or 2, provided that $R^1$, m' and n which are present in plurality in the same molecule may be the same or different, respectively, and a polymerizable functional group represented by the following formula (3):

(3)

wherein $R^3$ represents a hydrogen atom or an alkyl group having from 1 to 6 carbon atoms, $R^4$ represents a chained, branched and/or cyclic divalent group having from 1 to 10 carbon atoms, which may contain a hetero atom, and x represents 0 or an integer of from 1 to 10, provided that $R^3$, $R^4$ and x which are present in plurality in the same molecule may be the same or different, respectively, and a polymer-